United States Patent [19]

Konteatis et al.

[11] Patent Number: 5,614,370
[45] Date of Patent: Mar. 25, 1997

[54] ASSAY TO IDENTIFY HUMAN C5A ANTAGONISTS AND AGONISTS

[75] Inventors: Zenon Konteatis, South Orange; Salvatore J. Siciliano, East Brunswick; Martin S. Springer, Westfield, all of N.J.

[73] Assignee: Merck & Co., Inc., Rahway, N.J.

[21] Appl. No.: 215,137

[22] Filed: Mar. 18, 1994

[51] Int. Cl.$^6$ ..................................................... G01N 33/53
[52] U.S. Cl. ........................... 435/7.21; 435/7.1; 435/7.2; 435/7.24; 436/501; 436/518; 436/519; 436/544; 436/545
[58] Field of Search ........................... 435/7.1, 7.2, 7.21, 435/7.24; 436/501, 518, 519, 544, 545

[56] References Cited

U.S. PATENT DOCUMENTS

| | | | |
|---|---|---|---|
| 4,692,511 | 9/1987 | Hahn | 530/325 |
| 5,079,228 | 1/1992 | Cohen et al. | 514/12 |
| 5,177,190 | 1/1993 | Rollins et al. | 530/350 |
| 5,190,922 | 3/1993 | Luly et al. | 514/18 |
| 5,223,485 | 6/1993 | Kawai et al. | 514/16 |
| 5,250,564 | 10/1993 | Hirschmann et al. | 514/414 |

FOREIGN PATENT DOCUMENTS

| | | |
|---|---|---|
| WO90/09162 | 8/1990 | WIPO . |
| WO92/11858 | 7/1992 | WIPO . |
| WO92/12168 | 7/1992 | WIPO . |
| WO92/21361 | 12/1992 | WIPO . |
| WO94/07518 | 4/1994 | WIPO . |

OTHER PUBLICATIONS

PNAS, vol. 91, pp. 1214–1218 (1994) Siciliano et al.
Biochemical Pharmacology, vol. 45, No. 6, pp. 1289–1299 (1993) Deapeau et al.
*Biocactivities*, vol. 8, No. 1; pp. 1–2 (Apr. 1994).
S. A. Khan et al., XIth Int. Complement Workshop, No. 118, p. 42.
M. Kawai et al., J. Med. Chem., vol. 34; pp. 2068–2071 (1991).
M. Kawai et al., J. Med. Chem, vol. 35; pp. 220–223 (1992).
Y. S. Or et al., J. Med. Chem, vol. 35; pp. 402–406 (1992).
K. W. Mollison et al., Proc. Natl. Acad. Sci. USA, vol. 86; pp. 292–296, (Jan. 1989).
C. Gerard et al., J. Reticuloendothel. Soc., vol. 26; pp. 711–718 (1979).
D. E. Chenosweth & T. E. Hugli, Mol. Immun., vol. 17; pp. 151–161 (1980).
J. A. Ember et al., J. Immun., vol. 148 No. 10; pp. 3165–3173 (1992).

*Primary Examiner*—Lora M. Green
*Attorney, Agent, or Firm*—Mollie M. Yang; David L. Rose

[57] ABSTRACT

The invention is an assay, including a series of peptides, which allow screening for inhibitors of C5*a* binding targeted to the subsite on the C5*a* receptor occupied by the C-terminus of C5*a*. These peptides allow compound testing efforts to be targeted to this same subsite so that C5*a* agonists and antagonists can be identified. These peptides have much greater affinity (Ki<10 nM) than does the natural C-terminus of C5*a* (Ki=300 μM) and have been labeled to allow for detection of molecules which inhibit binding of these peptides at this receptor subsite. The invention is useful to develop agonists, partial agonists, and antagonists of C5*a*, and the invention includes compounds identified according to the method of this invention and methods of their use.

7 Claims, 8 Drawing Sheets

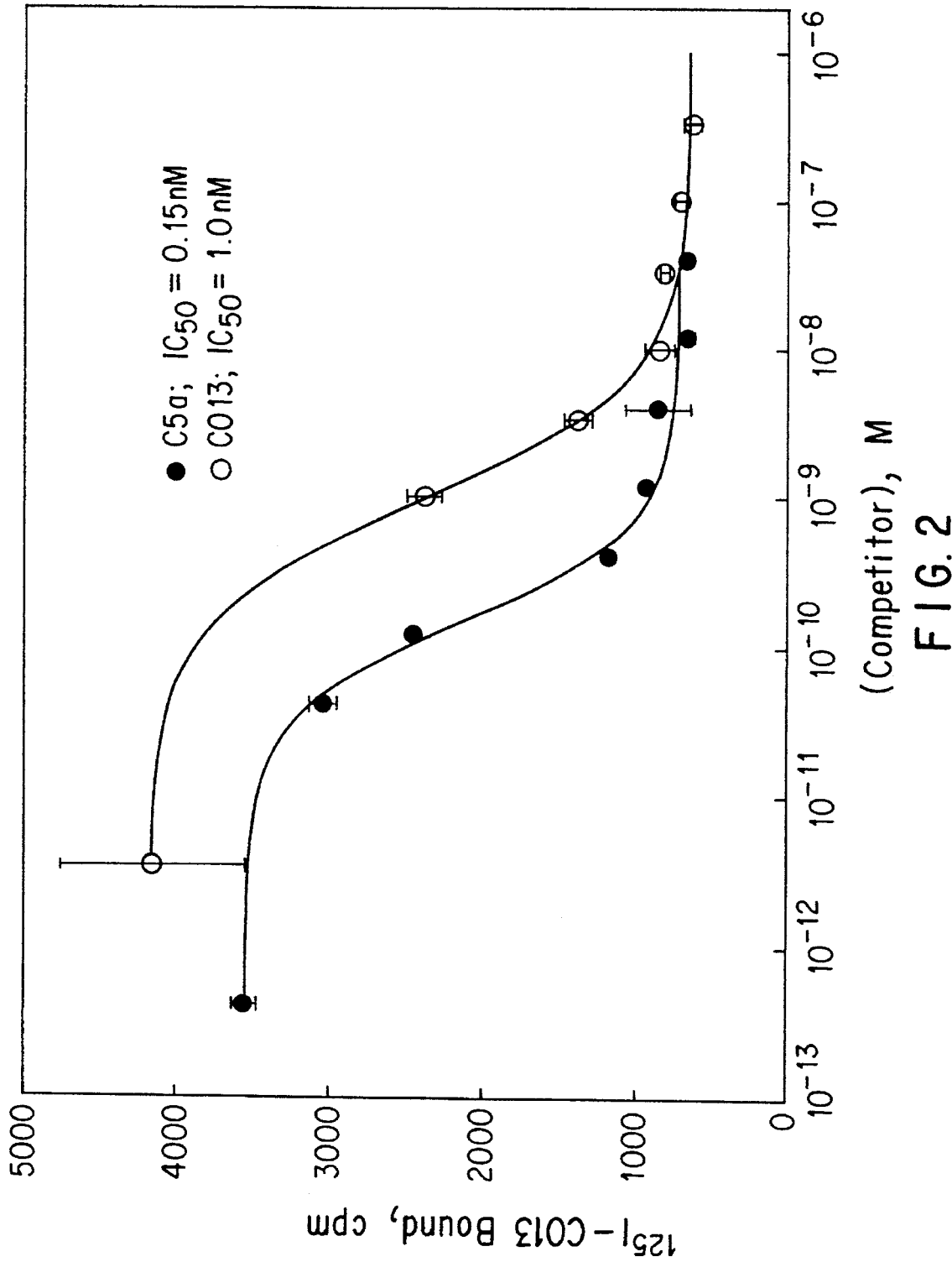

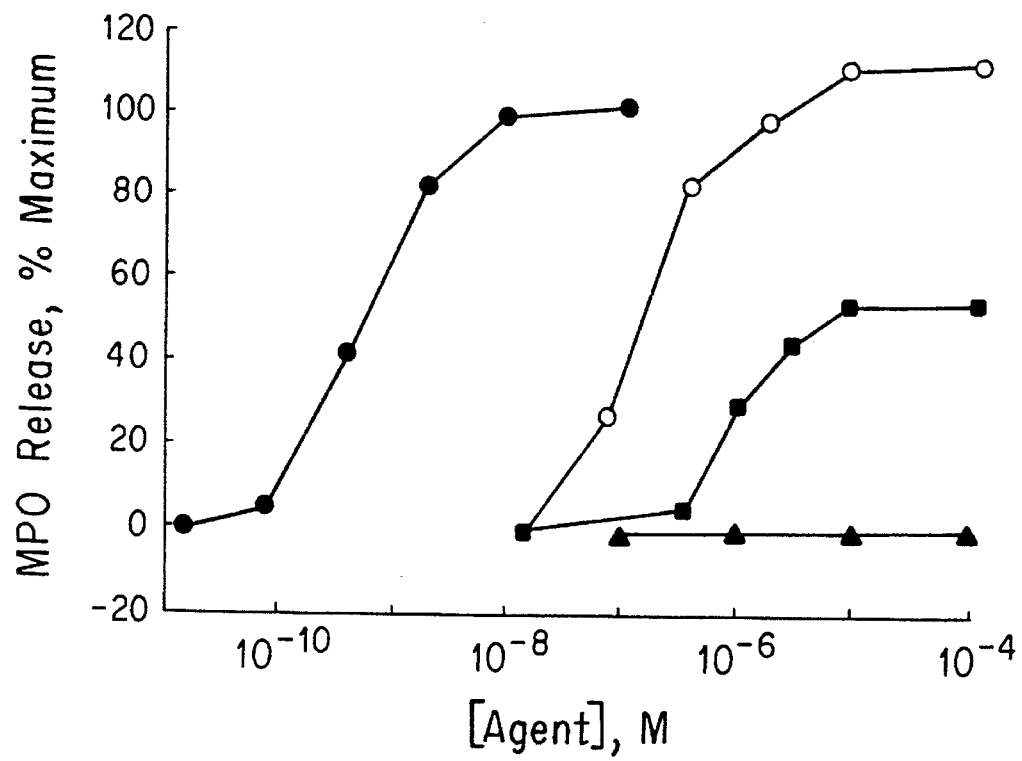
F I G. 5a
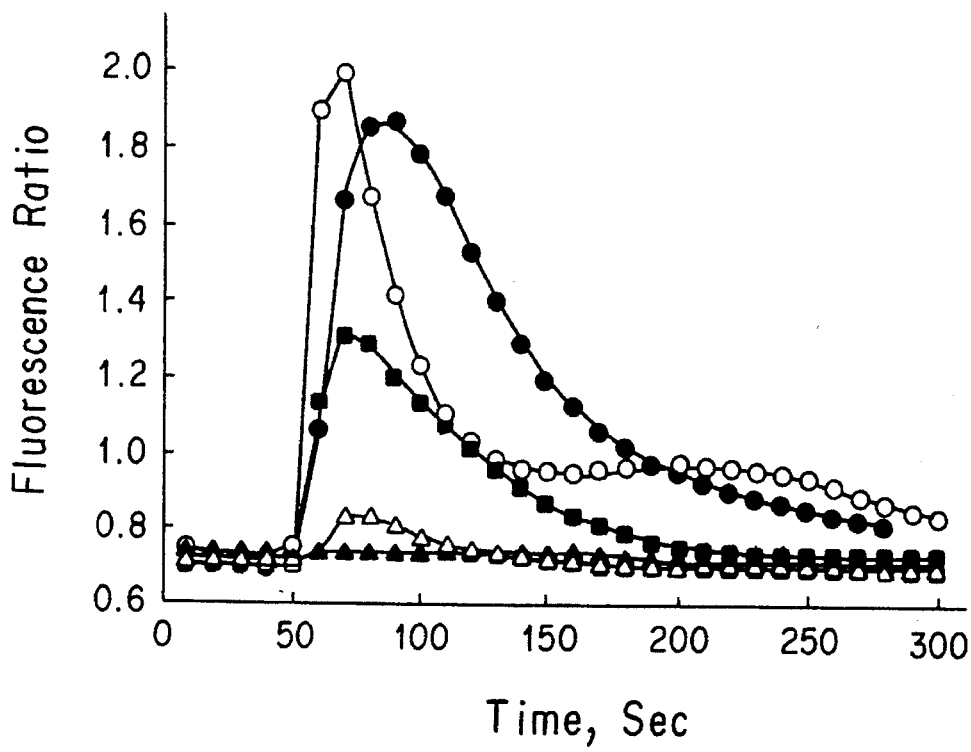
F I G. 5b

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
        ( A ) NAME/KEY: Modified-site
        ( B ) LOCATION: 1
        ( D ) OTHER INFORMATION: /label=125I
            / note= "Site of radioiodination."

( i x ) FEATURE:
        ( A ) NAME/KEY: Modified-site
        ( B ) LOCATION: 5
        ( D ) OTHER INFORMATION: /label=Cha
            / note= "cyclohexylalanine"

( i x ) FEATURE:
        ( A ) NAME/KEY: Modified-site
        ( B ) LOCATION: 6
        ( D ) OTHER INFORMATION: /label=Cha
            / note= "cyclohexylalanine"

( i x ) FEATURE:
        ( A ) NAME/KEY: Modified-site
        ( B ) LOCATION: 8
        ( D ) OTHER INFORMATION: /label=dPhe
            / note= "D-phenylalanine"

( x i ) SEQUENCE DESCRIPTION: SEQ ID NO:1:

Tyr   Phe   Lys   Ala   Xaa   Xaa   Leu   Phe   Arg
   1                            5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
        ( A ) NAME/KEY: Modified-site
        ( B ) LOCATION: 1
        ( D ) OTHER INFORMATION: /label=125-I
            / note= "Site of radioiodination"

( i x ) FEATURE:
        ( A ) NAME/KEY: Modified-site
        ( B ) LOCATION: 5
        ( D ) OTHER INFORMATION: /label=Cha
            / note= "cyclohexylalanine"

( i x ) FEATURE:
        ( A ) NAME/KEY: Modified-site
        ( B ) LOCATION: 8
        ( D ) OTHER INFORMATION: /label=dPhe
            / note= "D-phenylalanine"

( x i ) SEQUENCE DESCRIPTION: SEQ ID NO:2:

Tyr Phe Lys Ala Xaa Gly Leu Phe Arg
1               5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
        ( A ) NAME/KEY: Modified-site
        ( B ) LOCATION: 1
        ( D ) OTHER INFORMATION: /label=MePhe
            / note= "methyl-phenylalanine"

( i x ) FEATURE:
        ( A ) NAME/KEY: Modified-site
        ( B ) LOCATION: 4
        ( D ) OTHER INFORMATION: /label=dCha
            / note= "D-cyclohexylalanine"

( i x ) FEATURE:
        ( A ) NAME/KEY: Modified-site
        ( B ) LOCATION: 5
        ( D ) OTHER INFORMATION: /label=Cha
            / note= "cyclohexylalanine"

( i x ) FEATURE:
        ( A ) NAME/KEY: Modified-site
        ( B ) LOCATION: 6
        ( D ) OTHER INFORMATION: /label=dArg
            / note= "D-arginine"

( x i ) SEQUENCE DESCRIPTION: SEQ ID NO:3:

Phe Lys Pro Xaa Xaa Arg
1               5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
        ( A ) NAME/KEY: Modified-site
        ( B ) LOCATION: 1
        ( D ) OTHER INFORMATION: /label=125-I
            / note= "site of radioiodination"

( i x ) FEATURE:
        ( A ) NAME/KEY: Modified-site
        ( B ) LOCATION: 5
        ( D ) OTHER INFORMATION: /label=dCha
            / note= "D-cyclohexylalanine"

(ix) FEATURE:
        (A) NAME/KEY: Modified-site
        (B) LOCATION: 6
        (D) OTHER INFORMATION: /label=Cha
                / note= "cyclohexylalanine"

(ix) FEATURE:
        (A) NAME/KEY: Modified-site
        (B) LOCATION: 7
        (D) OTHER INFORMATION: /label=dArg
                / note= "D-arginine"

(xi) SEQUENCE DESCRIPTION: SEQ ID NO:4:

Tyr  Phe  Lys  Pro  Xaa  Xaa  Arg
    1                    5

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 1
        (D) OTHER INFORMATION: /label=R1
                / note= "amino acid which permits labeling,
                preferably Tyr or 3-(4-hydroxyphenyl)propionyl
            (BH)"

(ix) FEATURE:
        (A) NAME/KEY: Modified-site
        (B) LOCATION: 2
        (D) OTHER INFORMATION: /label=R2
                / note= "peptide bond, single amino acid, or
                several amino acids"

(ix) FEATURE:
        (A) NAME/KEY: Modified-site
        (B) LOCATION: 5
        (D) OTHER INFORMATION: /label=R3
                / note= "Ala, Pro, Pip, N-MeAla, Tic,
                wherein Tic is tetrahydroisoquinolyl, and
                Pip is homoproline"

(ix) FEATURE:
        (A) NAME/KEY: Modified-site
        (B) LOCATION: 6
        (D) OTHER INFORMATION: /label=R4
                / note= "L-Cha or D-Cha, wherein Cha is
                cyclohexylalanine"

(ix) FEATURE:
        (A) NAME/KEY: Modified-site
        (B) LOCATION: 7
        (D) OTHER INFORMATION: /label=R5
                / note= "Gly, Cha, Leu, Phe, Nal, Trp, wherein Nal
                is 1- naphthylalanine"

(ix) FEATURE:
        (A) NAME/KEY: Modified-site
        (B) LOCATION: 8
        (D) OTHER INFORMATION: /label=R6
                / note= "L- or D-aliphatic or aromatic
                amino acid, preferably Leu, d-Arg, Trp, or D-Leu"

(ix) FEATURE:
        (A) NAME/KEY: Modified-site (B) LOCATION: 9
(D) OTHER INFORMATION: /label=X1
/ note= "aliphatic or aromatic D-amino acid when
X2 is L-Arg, and R6 is an L-aliphatic or aromatic
amino acid such as L-Leu or L-Trp; X1 is preferably
D-Phe or D- Ala; X1 is absent when R6 is D-Arg, and
is D-Arg when R6 is a D-aliphatic or D-aromatic
amino acid such as D-Leu or D-Trp"

(ix) FEATURE:
(A) NAME/KEY: Modified-site
(B) LOCATION: 10
(D) OTHER INFORMATION: /label=X2
/ note= "L-Arg or not present"

(xi) SEQUENCE DESCRIPTION: SEQ ID NO:5:

Xaa Xaa Phe Lys Xaa Xaa Xaa Xaa Xaa Xaa
1                 5                           10

(2) INFORMATION FOR SEQ ID NO:6:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
(A) NAME/KEY: Modified-site
(B) LOCATION: 2
(D) OTHER INFORMATION: /label=Cha
/ note= "Cyclohexylalanine"

(ix) FEATURE:
(A) NAME/KEY: Modified-site
(B) LOCATION: 5
(D) OTHER INFORMATION: /label=dPhe
/ note= "D-phenylalanine"

(xi) SEQUENCE DESCRIPTION: SEQ ID NO:6:

Ala Xaa Gly Leu Phe Arg
1                 5

(2) INFORMATION FOR SEQ ID NO:7:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
(A) NAME/KEY: Modified-site
(B) LOCATION: 2
(D) OTHER INFORMATION: /label=dCha
/ note= "D-cyclohexylalanine"

(ix) FEATURE:
(A) NAME/KEY: Modified-site
(B) LOCATION: 3

(D) OTHER INFORMATION: /label=Cha
                        / note= "cyclohexylalanine"

(ix) FEATURE:
                    (A) NAME/KEY: Modified-site
                    (B) LOCATION: 4
                    (D) OTHER INFORMATION: /label=dArg
                        / note= "D-arginine"

(xi) SEQUENCE DESCRIPTION: SEQ ID NO:7:

Pro Xaa Xaa Arg
        1

(2) INFORMATION FOR SEQ ID NO:8:

(i) SEQUENCE CHARACTERISTICS:
                    (A) LENGTH: 4 amino acids
                    (B) TYPE: amino acid
                    (C) STRANDEDNESS: single
                    (D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
                    (A) NAME/KEY: Modified-site
                    (B) LOCATION: 1
                    (D) OTHER INFORMATION: /label= N- MeAla
                        / note= "N-methylalanine"

(ix) FEATURE:
                    (A) NAME/KEY: Modified-site
                    (B) LOCATION: 2
                    (D) OTHER INFORMATION: /label=dCha
                        / note= "D-cyclohexylalanine"

(ix) FEATURE:
                    (A) NAME/KEY: Modified-site
                    (B) LOCATION: 4
                    (D) OTHER INFORMATION: /label=dArg
                        / note= "D-arginine"

(xi) SEQUENCE DESCRIPTION: SEQ ID NO:8:

Ala Xaa Leu Arg
        1

(2) INFORMATION FOR SEQ ID NO:9:

(i) SEQUENCE CHARACTERISTICS:
                    (A) LENGTH: 4 amino acids
                    (B) TYPE: amino acid
                    (C) STRANDEDNESS: single
                    (D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
                    (A) NAME/KEY: Modified-site
                    (B) LOCATION: 1
                    (D) OTHER INFORMATION: /label=Tic
                        / note= "tetrahydroisoquinolyl"

(ix) FEATURE:
                    (A) NAME/KEY: Modified-site
                    (B) LOCATION: 2

( D ) OTHER INFORMATION: /label=dCha
/ note= "D-cyclohexylalanine"

( i x ) FEATURE:
( A ) NAME/KEY: Modified-site
( B ) LOCATION: 4
( D ) OTHER INFORMATION: /label=dArg
/ note= "D-arginine"

( x i ) SEQUENCE DESCRIPTION: SEQ ID NO:9:

Xaa Xaa Phe Arg
1

( 2 ) INFORMATION FOR SEQ ID NO:10:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
( A ) NAME/KEY: Modified-site
( B ) LOCATION: 1
( D ) OTHER INFORMATION: /label=Tic
/ note= "tetrahydroisoquinoline carboxyllic acid"

( i x ) FEATURE:
( A ) NAME/KEY: Modified-site
( B ) LOCATION: 2
( D ) OTHER INFORMATION: /label=dCha
/ note= "D-cyclohexylalanine"

( i x ) FEATURE:
( A ) NAME/KEY: Modified-site
( B ) LOCATION: 3
( D ) OTHER INFORMATION: /label=Nal
/ note= "1-naphthylalanine"

( i x ) FEATURE:
( A ) NAME/KEY: Modified-site
( B ) LOCATION: 4
( D ) OTHER INFORMATION: /label=dArg
/ note= "D-arginine"

( x i ) SEQUENCE DESCRIPTION: SEQ ID NO:10:

Xaa Xaa Xaa Arg
1

( 2 ) INFORMATION FOR SEQ ID NO:11:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
( A ) NAME/KEY: Modified-site
( B ) LOCATION: 1

(D) OTHER INFORMATION: /label=Tic
/ note= "tetrahydroisoquinoline carboxyllic acid"

(ix) FEATURE:
(A) NAME/KEY: Modified-site
(B) LOCATION: 2
(D) OTHER INFORMATION: /label=dCha
/ note= "D-cyclohexylalanine"

(ix) FEATURE:
(A) NAME/KEY: Modified-site
(B) LOCATION: 4
(D) OTHER INFORMATION: /label=dArg
/ note= "D-arginine"

(xi) SEQUENCE DESCRIPTION: SEQ ID NO:11:

Xaa Xaa Trp Arg
1

(2) INFORMATION FOR SEQ ID NO:12:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
(A) NAME/KEY: Modified-site
(B) LOCATION: 1
(D) OTHER INFORMATION: /label=Tic
/ note= "tetrahydroisoquinolinyl"

(ix) FEATURE:
(A) NAME/KEY: Modified-site
(B) LOCATION: 2
(D) OTHER INFORMATION: /label=Cha
/ note= "cyclohexylalanine"

(ix) FEATURE:
(A) NAME/KEY: Modified-site
(B) LOCATION: 5
(D) OTHER INFORMATION: /label=dAla
/ note= "D-alanine"

(xi) SEQUENCE DESCRIPTION: SEQ ID NO:12:

Xaa Xaa Gly Trp Ala Arg
1               5

(2) INFORMATION FOR SEQ ID NO:13:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
(A) NAME/KEY: Modified-site
(B) LOCATION: 1

(D) OTHER INFORMATION: /label=BH
/ note= "either the natural phenylalanine amino
terminus or the Bolton-Hunter modified peptide
having the group 3-(p-hydroxyphenyl)propionyl group (ix) FEATURE:
  (A) NAME/KEY: Modified-site
  (B) LOCATION: 4
  (D) OTHER INFORMATION: /label=dCha
    / note= "D-cyclohexylalanine"

(ix) FEATURE:
  (A) NAME/KEY: Modified-site
  (B) LOCATION: 6
  (D) OTHER INFORMATION: /label=dArg
    / note= "D-arginine"

(xi) SEQUENCE DESCRIPTION: SEQ ID NO:13:

Phe Lys Pro Xaa Trp Arg
1               5

(2) INFORMATION FOR SEQ ID NO:14:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
    (A) NAME/KEY: Modified-site
    (B) LOCATION: 1
    (D) OTHER INFORMATION: /label=NMePhe
      / note= "N-methyl-phenylalanine"

(ix) FEATURE:
    (A) NAME/KEY: Modified-site
    (B) LOCATION: 3
    (D) OTHER INFORMATION: /label=R7
      / note= "Pro or Tic"

(ix) FEATURE:
    (A) NAME/KEY: Modified-site
    (B) LOCATION: 4
    (D) OTHER INFORMATION: /label=dCha
      / note= "D-cyclohexylalanine"

(ix) FEATURE:
    (A) NAME/KEY: Modified-site
    (B) LOCATION: 5
    (D) OTHER INFORMATION: /label=R8
      / note= "Phe, Nal, Trp or a more aromatic amino
      acid derivative"

(ix) FEATURE:
    (A) NAME/KEY: Modified-site
    (B) LOCATION: 6
    (D) OTHER INFORMATION: /label=dArg
      / note= "D-arginine"

(xi) SEQUENCE DESCRIPTION: SEQ ID NO:14:

Phe Lys Xaa Xaa Xaa Arg
1               5

(2) INFORMATION FOR SEQ ID NO:15:

(i) SEQUENCE CHARACTERISTICS:
    (A) LENGTH: 6 amino acids (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
       (A) NAME/KEY: Modified-site
       (B) LOCATION: 1
       (D) OTHER INFORMATION: /label=NMePhe
           / note= "N-methyl-phenylalanyl"

(ix) FEATURE:
       (A) NAME/KEY: Modified-site
       (B) LOCATION: 4
       (D) OTHER INFORMATION: /label=dCha
           / note= "D-cyclohexylalanyl"

(ix) FEATURE:
       (A) NAME/KEY: Modified-site
       (B) LOCATION: 5
       (D) OTHER INFORMATION: /label=X
           / note= "Nal, Trp, or a more aromatic amino acid
           derivative"

(ix) FEATURE:
       (A) NAME/KEY: Modified-site
       (B) LOCATION: 6
       (D) OTHER INFORMATION: /label=dArg
           / note= "D-arginine"

(xi) SEQUENCE DESCRIPTION: SEQ ID NO:15:

Phe  Lys  Pro  Xaa  Xaa  Arg
   1                 5

ASSAY TO IDENTIFY HUMAN C5A ANTAGONISTS AND AGONISTS

BACKGROUND OF THE INVENTION i. Field of the Invention

This invention relates to an assay to identify compounds useful as C5a antagonists. The invention also comprises C5a antagonists and uses thereof as anti-inflammatory agents and as immunoregulants.

ii. Background

The importance of the C5a receptor finds its origin in its relationship with complement derived C5a and its role in the overall immune response. The complement system is a complex group of proteins present in body fluids that, working together with antibodies or other factors, plays an important role in mediation of immune, allergic, immunochemical and immunopathological reactions. Activation of the complement system can result in a wide range of reactions such as lysis of various kinds of cells, bacteria, protozoa, inactivation of viruses, and the direct mediation of inflammatory processes. Through the hormone-like activity of several of its components, the complement system recruits and enlists the participation of other humoral and cellular effector systems. These in turn induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. In a sequential series of activation steps (the "complement cascade"), proteins are activated and then combine with additional proteins to form complexes that cleave and activate still other proteins in the system. The sequential activation of these proteins follows two main pathways, the classical pathway and the alternative pathway. Both pathways use a common terminal trunk that leads to cell lysis or virus inactivation.

The classical pathway can be activated by antigen-antibody complexes, aggregated immuno-globulins and non-immunological substances such as DNA and trypsin-like enzymes. The classical pathway includes activation of $C_1$, $C_4$, $C_2$ and $C_3$ molecules. These components can be grouped into two functional units: $C_1$ or recognition unit; and $C_4$, $C_2$ and $C_3$ or activation unit. Five additional components denominated $C_5$, $C_6$, $C_7$, $C_8$, and $C_9$ define the membrane attack unit forming the terminal trunk common to both pathways.

The acute inflammatory response depends on the attraction of phagocytic polymorphonuclear leukocytes (PMN's) to the site of microbial invasion by a chemotactic stimulus. The C5a component is pivotal to the effectuation of this response in humans.

C5a is a 74 amino acid protein derived from the fifth component of serum complement during complement activation. C5a is known to mediate various pathological conditions, chronic inflammation, acute pulmonary disorders and even the metastatic spread of cancerous tumors. C5a is chemotactic for neutrophils, monocytes, macrophages, eosinophils and basophils. Thus, this serum factor is an important attractant to leukocytes and is crucial to their accumulation in vivo at sites of immunologic injury.

Leukocytes accumulated at a site of inflammation release granular contents, various hydrolytic enzymes and other cytotoxic components into the extracellular spaces in a process referred to as degranulation, as a result of which the surrounding tissue is damaged.

Numerous chronic inflammatory diseases are thought to involve the aberrant presence of C5a in tissue. Rheumatoid arthritis, osteoarthritis and psoriasis are a few examples. The lung is particularly vulnerable; excess C5a in circulation or in the lung can result in aggregation and migration of leukocytes into this organ. This can lead to microvascular occlusion, endothelial damage and subsequent edema. In *J. Amer. Med. Soc.*, 244, 199 (1980), Hammerschmidt suggested that noncardiac pulmonary edema associated with blood transfusion and hemodialysis depend on an aberrant increase in circulating C5a.

In view of the above, and as generally supported in the literature, it is believed that compounds which could antagonize the binding of C5a to its receptor on effector cells would be useful in the treatment of a wide variety of C5a mediated diseases such as acute inflammatory response, including acute respiratory distress syndrome (ARDS), and anaphylactic shock; chronic inflammation including rheumatoid arthritis, osteoarthritis and psoriasis and metastatic spread of cancerous tumor. See Yancy, K.B., Review—Biological Properties of Human C5a: selected in vitro and in vivo studies, *Clin. Exp. Immunol.* (1988) 71, 207–210, and references cited therein.

Previous attempts to develop antagonists of C5a utilized an assay to screen for inhibitors of the binding of the intact C5a molecule. The rational design of a useful antagonist requires detailed knowledge of the important receptor-ligand interactions. The binding subunit of the C5a receptor has been cloned and shown to be a member of G protein-coupled receptor superfamily (Gerard, N. P. and Gerard, C. (1991) *Nature* 349, 614–617; Boulay, F., Mery, L., Tardif, M., Brouchon, L. and Vignais, P. (1991) *Biochemistry* 30, 2993–2999). The region of this molecule which interacts with C5a consists of two subsites. The first is in the binding subunit's N-terminus, and although the second subsite has not been definitely localized, it appears to lie between the transmembrane spanning helices.

Similarly, site-directed mutagenesis and studies with peptide analogs of C5a have identified two regions on this molecule which are important for binding to the receptor. The first is in the core of the C5a molecule, centered around Arg40 (Mollison, K. W., Mandecki, W., Zuiderweg, E. R. P., Fayer, L., Fey, T. A., Kranuse, R. A., Conway, R. G., Miller, L., Edalji, R. P., Shallcrss, M. A., Lane, B., Fox, J. L., Greer, J. and Carter, G. W. (1989) *Proc. Natl. Acad. Sci. USA* 86, 292–297), while the second is contained in the C-terminal eight amino acids (Kawai, M., Or, Y. S., Wiedman, P. E., Luly, J. and Moyer, M. (1990) *World Intellectual Property Organization*, Publication Number WO 90/09162; Kawai, M., Quincy, D., A., Lane, B., Mollison, K., W., Luly, J., R. and Carter, G., W. (1991) *Journal of Medicinal Chemistry* 34, 2068–2071 ). A synthetic peptide consisting of these eight residues inhibits C5a binding with a Ki=300 μM, and has agonist properties. Subsequent structure activity studies have produced analogs with much higher affinities while reducing the size of the peptides from eight to six residues (Mollison, K. W., Krause, R. A., Fey, T. A., Miller, L., Wiedeman, P. e., Kawai, M., Lane, B., Luly, J. R. and Carter, G. W. (1992) FASEB J. 6, A2058; Kawai, M., Lane, B., Mollison, K. W., Luly, J. R. and Carter, G. W. (1991) *12th Amer. Peptide Symposium*, poster #525). However, efforts at generating antagonists of C5a have so far been unsuccessful. The one partial exception is the peptide NMeF—K—P-dCha-F-dR (NMeF is N-methyl phenylalanine, and Cha is cyclohexylalanine), which while not an antagonist, appears to have reduced agonist properties. For example, Mollison et. al. (Mollison, K. W., Krause, R. A., Fey, T. A., Miller, L., Wiedeman, P. e., Kawai, M., Lane, B., Luly, J. R. and Carter, G. W. (1992) *FASEB J.* 6, A2058) have reported that this peptide evokes only a small chemokinetic response, and is totally devoid of degranulating activity. Further, Drapeau et. al. (Drapeau, G., Brochu, S., Godin, D., Levesque, L., Rioux, F. and Marceau, F. (1993) *Biochem. Pharm.* 45, 1289–1299) found that the peptide failed to stimulate superoxide release from neutrophils, although it behaved as an agonist in other assays.

The instant inventors have discovered that intact C5a binds to its receptor by interaction at two physically distinct loci. This, at least in part, explains why the existing assays could not distinguish at which locus potentially inhibitory compounds act. In order to develop inhibitors which block the interaction of the C-terminus of C5a with its receptor, we have developed high affinity, labeled peptides to allow our research to focus on this one locus. Prior to the current invention such specificity was not possible.

Peptides from the COOH terminus of C5a have been reported. However, peptides disclosed in these publications have not been used according to the method of the instant invention, and there have not been reports of compounds that exhibit full C5a antagonism at submicromolar concentrations. Thus, see:

Abbott-WO 90/90162; WO 9212168-A1; WO 92/21361 described anaphylatoxin receptor ligands; see also U.S. Pat. Nos. 5,190,922 and 5,223,485, both assigned to Abbott and essentially equivalent to the international publications in content;

Kahn, S. A. et al. Complement 2, 42 (1985) described a 21-residue peptide based on the C5a COOH-terminus;

Kawai, M., et al. *J. Med. Chem.*, 35, 2068 (1991) described a C-terminal C5a octapeptide which retained receptor binding activity; Kawai, M. et al. *J. Med Chem.*, 35, 220 (1992) described modified C5a COOH-terminal octapeptide analogs having a Ki for C5a binding of 1–3 µm;

Mollison et al. *Proc. Nat. Acad. Sci.*, 86, 292 (1989) described a Phe for His67 substituted C5a peptide with a Ki of 0.26 µm;

Gerard, C. Get al. *J. Reticuloendothel. Soc.*, 26, 711 (1979) identified the C5a COOH-terminus as critical to activity of C5a as a neutrophil chemotactic agent;

Chenoweth, D. E. *Mol Immunol.*, 17, 151 (1980) identified the C-terminal portion of C5a as important for modulating neutrophil receptor-ligand interaction;

Ember J. A. et al. *J. Immuol.*, 148 3155 (1992) confirmed the increased potency of Phe for His67 substituted C-terminal analogs.

Mollison et al. *PNAS USA*, 86, 292 (1989) identified receptor binding residues in intact C5a.

A detailed structure/activity relationship for C-terminal peptide analogs of C5a has emerged from studies in a number of laboratories (Kawai, M., Or, Y. S., Wiedman, P. E., Luly, J. and Moyer, M. (1990) *World Intellectual Property Organization*, Publication Number WO 90/09162; Kawai, M., Quincy, D., A., Lane, B., Mollison, K., W., Luly, J., R. and Carter, G., W. (1991) *Journal of Medicinal Chemistry* 34, 2068–2071; Mollison, K. W., Krause, R. A., Fey, T. A., Miller, L., Wiedeman, P. e., Kawai, M., Lane, B., Luly, J. R. and Carter, G. W. (1992) *FASEB J.* 6, A2058; Kawai, M., Lane, B., Mollison, K. W., Luly, J. R. and Carter, G. W. (1991) *12th Amer. Peptide Symposium*, poster #525; Ember, J. A., Sanderson, S. D., Taylor, S. M., Kawahara, M. and Hugli, T. E. (1992) *J. Immunol.* 148, 3165–3173). The minimum size of the peptides has been reduced to 6 residues, as contrasted to 74 in the natural molecule, and analogs with affinities as high as 1–10 nM have been reported. However, all of these molecules retain strong agonist properties. In U.S. Pat. No. 4,692,511, a series of peptides were reported to act as competitive antagonists for the C5a receptor. The peptides were centered around the Asp-Gly-Ala tripeptide at positions 24, 25, and 26 in the naturally occurring C5a molecule. No binding or inhibition data were presented. However, it is manifest from the work we report herein that those purported antagonists were low-affinity molecules with Ki's in the micromolar and higher range. As such, those peptides could not be useful as specific C5a receptor antagonists. As we teach herein, them are two sites for C5a binding to its receptor and peptides disclosed in the 4,692,511 Patent would bind to the external, low-affinity site of the receptor.

Since C5a is an important inflammatory mediator, the development of an antagonist is of considerable therapeutic interest. In this patent disclosure we report that increasing the aromaticity of the residue in position 5 of C5a COOH-terminal hexapeptide analogs leads to a progressive loss of agonism, and we disclose the first full C5a antagonist active at submicromolar concentrations.

SUMMARY OF THE INVENTION

The invention is a method, including a series of peptides, which allows screening for inhibitors of C5a binding targeted to the subsite on the receptor occupied by the C-terminus of C5a. The peptides employed in the instant assay exhibit much greater affinity (Ki<10 nM) than does the natural C-terminus of C5a (Ki=300 µM) and have been labeled to allow for detection of molecules which inhibit binding of these peptides at this receptor subsite. Because the method is a powerful method for identifying C5a receptor binding compounds, it is useful in the identification and development of agonists, partial agonists, and antagonists of C5a. The method has permitted identification of the first full C5a antagonist with submicromolar affinity for the C5a receptor. We report hexapeptide analogs of the form NMe-Phe-Lys-Pro-dCha-X-dArg in which increasing aromaticity at the position shown as "X" leads to a progressive loss of agonism with little change in binding affinity. The different responses induced by C5a are lost in the order: degranulation before $Ca^{2+}$-flux before chemotaxis. We also describe the first full antagonist of C5a, as the peptide in which X=Trp. This peptide is not only devoid of all agonist properties, it also inhibits C5a induced degranulation and C5a stimulated G protein activation.

BRIEF DESCRIPTION OF THE DRAWINGS

FIG. 2. Competition binding curve using $^{125}$I-labeled C013 peptide and unlabeled C013 peptide and unlabeled C5a.

FIG. 3A and 3B. (A) Competition binding curve using $^{125}$I-labeled intact C5a and unlabeled C064 peptide and unlabeled C5a. (B) Competition binding curve using $^{125}$I-labeled C064 and unlabeled C064 peptide and unlabeled C5a.

(B) Competition binding curve using $^{125}$I-labeled intact C5a and unlabeled C028 peptide in the presence and absence of protease secreting cells.

(C) Competition binding curve using $^{125}$I-labeled intact C5a and unlabeled C013 and C028 peptides in the presence and absence of protease secreting cells in the presence or absence of protease inhibitor.

FIG. 5A and 5B. Degranulation and $Ca^{2+}$ responses to the hexapeptides. Human neutrophils were examined for their ability to respond to C5a (●), C028 (O), C026 (■), C061(Δ), and C089 (▲). Panel A shows the concentration dependencies for degranulation as measured by MPO release. The $ED_{50}$'s for the degranulation are: C5a, 0.5 nM; C028, 0.2 μM; C026, 1 μM. C5a, maximally, released 57% of the total cellular content of MPO. The ability of these molecules to elicite a $Ca^{2+}$-flux is shown in B. The concentrations used for C028 (10 μM), C026 (10 μM), C061 (100 μM) are those which produce a maximal flux. A saturating concentration was also used for C5a (1 nM). The concentration used for C089 was 100 μM.

Figure 6A:
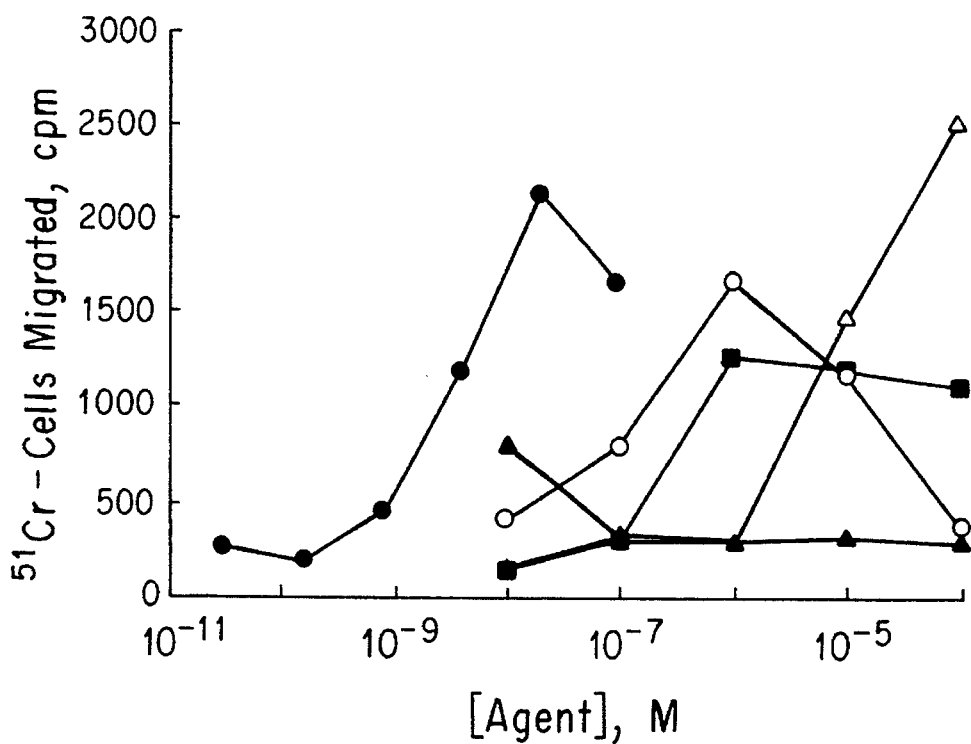
Figure 6B:
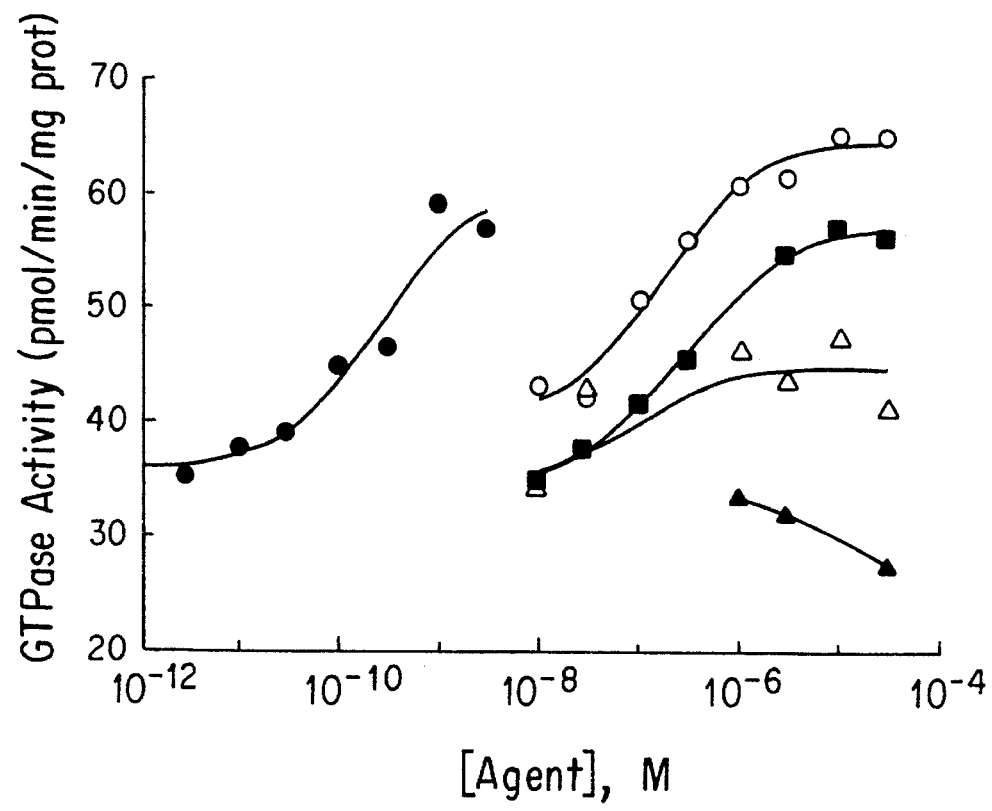

FIG. 6A and 6B. Chemotaxis and G protein activation elicited by the hexapeptides. The chemotactic response of human neutrophils to C5a (●), C028 (O), C026 (■), C061(Δ), and C089 (▲) is shown in A. G protein activation was assessed by measuring the stimulation of GTPase activity in human neutrophil membranes in response to C5a (●), C028 (O), C026 (■), C061(Δ), and C089 (▲) as shown in panel B.

Figure 7A:
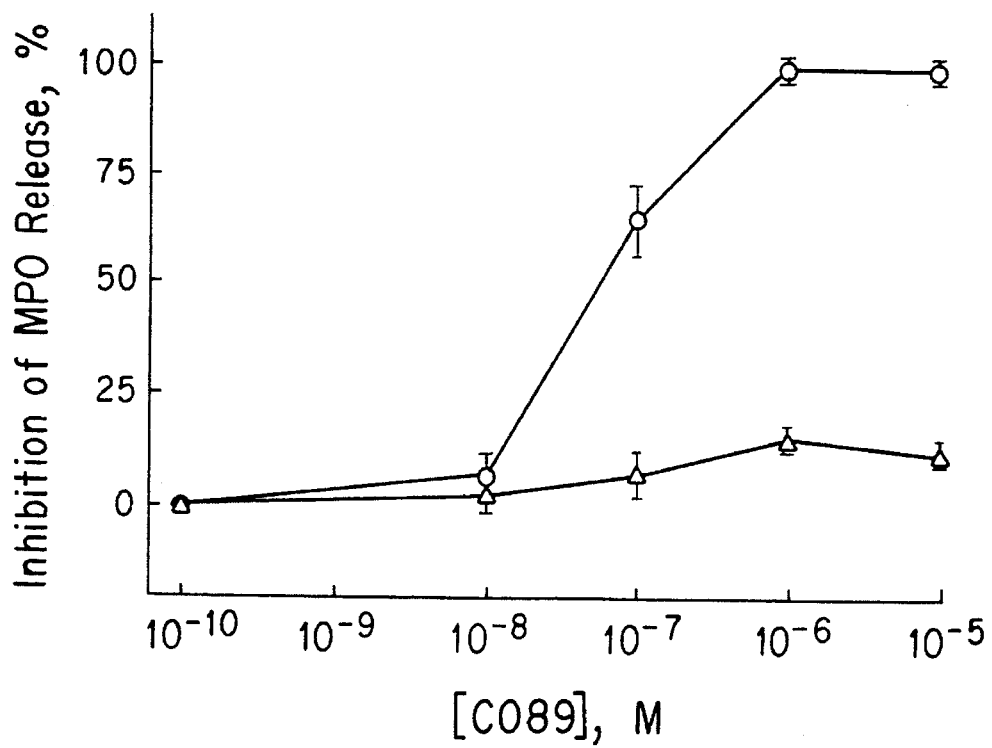
Figure 7B:
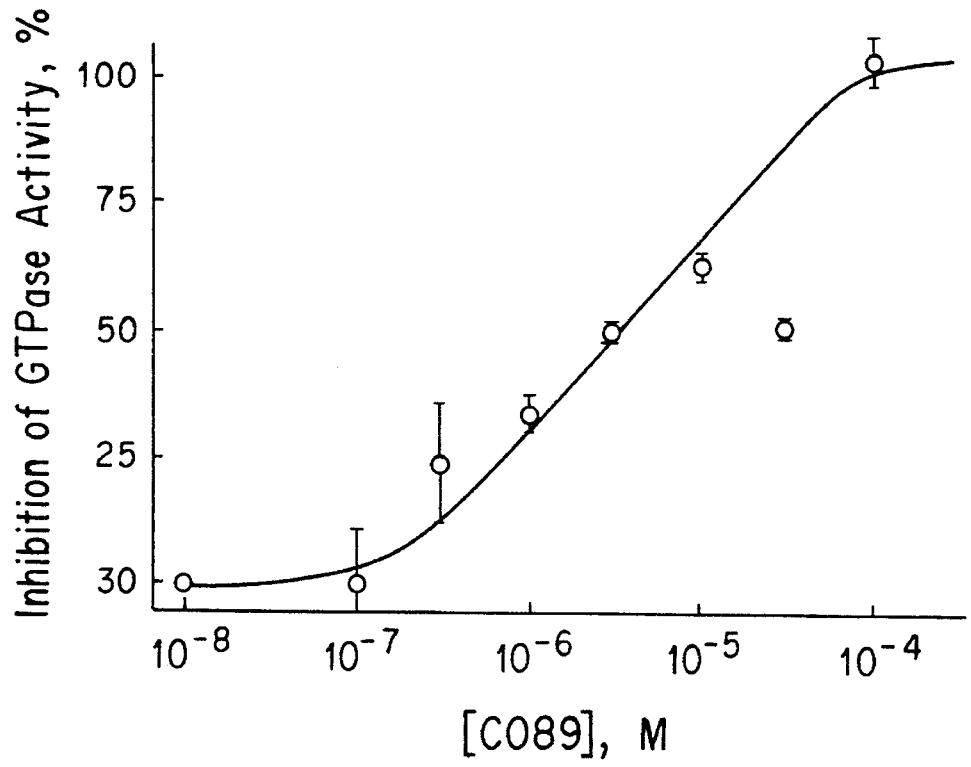

FIG. 7A and 7B. C089 is a C5a antagonist. The ability of C089 to inhibit C5a induced degranulation from human neutrophils is shown in A. Cells pre-incubated with the indicated concentration of C089 and then challenged with either 0.4 nM C5a (O), or 8 nM IL-8 (Δ) as a specificity control. These concentrations of the stimulating agents released 22% and 19% of the total cellular MPO, respectively. The ability of C089 to inhibit the increase in GTPase activity in human neutrophil membranes evoked by 3 nM C5a is shown in B. In the absence of C089 3 nM C5a increased GTPase activity from 46 to 64 pmol/min/mg protein.

DETAILED DESCRIPTION OF THE INVENTION

This invention relates to an assay for C5a antagonists, agonists, and partial agonists. It also relates to a method of treating C5a mediated diseases comprising administering to a patient in need of such treatment of non-toxic, C5a inhibitorily effective amounts of compounds identified according to this method.

A series of peptides are disclosed which enable identification of compounds which inhibit binding of C5a to its cellular receptor. The method is specific to C5a binding at the subsite on the receptor occupied by the C-terminus of C5a. Thus this method employs peptides which allow identification of C5a inhibitors, and thereby, identification of agonists and antagonists. These peptides have much greater affinity (Ki<10 nM) than does the natural C-terminus of C5a (Ki=300 μM) and have been labeled to allow for detection of molecules which inhibit binding of these peptides at this receptor subsite. This patent disclosure provides compounds which display full C5a receptor antagonism at submicromolar concentrations.

Prior art methods for identifying compounds exhibiting C5a receptor binding affinity involved the use of the intact C5a molecule. The instant inventors have discovered that the weakness with that method is that it does not discriminate between low affinity (Ki>1 μM) and higher affinity (Ki<1 μM) ligands. Thus, the task of identifying high affinity ligands was unmanageable, as large numbers of low affinity inhibitors were identified. In addition, the instant inventors have discovered the basis of this limitation to the prior art method. We have been able to demonstrate that the binding of C5a to its receptor is more complex than the binding, for example, of catecholamines to the β-adrenergic receptor. C5a binds both to the N-terminal portion of its cellular receptor and, in addition, the COOH-terminal portion of C5a interacts with another receptor site which may be localized inside the cell membrane. The N-terminal site depends on low-affinity, low-specificity ionic interactions, while the second binding site is a much higher affinity, and therefore much more specific binding site. This two-site binding model is confirmed by studies in which the binding at these two sites are uncoupled. For example, the weak ($IC_{50=3}$ μM) C5a antagonist L-584,020 [T.J. Lanza, et al., J. Med. Chem. 3.5:252–258 (1992)]has little effect on the binding of C5a COOH-terminal peptides.

As a result of this discovery, we have identified another weakness of the prior art method for discovery of C5a antagonists: ligands which can ionically interact with the N-terminus of the C5a receptor can also interact ionically with other receptors. Thus, we have found that low affinity C5a inhibitors, such as L-584,020, which interact at the amino terminus of the C5a receptor, also inhibit the interleukin-8 (IL-8) receptor. Thus, prior art methods identified C5a antagonists lacking in the requisite level of specificity for use in C5a antagonist therapeutic regimens.

While C5a COOH-terminal peptides exhibiting submicromolar affinity for the C5a receptor have been identified (see background section above), the implications of the two site binding of C5a were not fully appreciated heretofore. Thus, the instant inventors discovered the requirement for directing identification efforts at the COOH terminus of C5a, and using competition with intact C5a and other biological or functional assays only in a second step so as to confirm the biological activity of the compounds identified according to the method of the instant invention.

Once compounds have initially been identified according to the instant method and once inhibition of intact C5a binding has been confirmed, they may be further tested in a series of in vitro and in vivo assays. These methods are well known in the art. For example, neutrophil degranulation, $Ca^{++}$flux, chemotaxis, GTPase and GTPγ-S binding assays are all well known in the art. These assays measure the functional sequelae of C5a activation of its receptor through one or possibly more than one "G-protein". Thus, an additional utility of the instant method and compounds identified by this method, is as a method for dissection of the intracellular processes involved in C5a receptor coupled G-protein induced signal transduction.

In the method of this invention, compounds with C5a receptor antagonist, agonist, and partial agonist activity are identified by their ability to inhibit binding of high affinity peptides to the C5a receptor. Therefore, compounds exhibiting submicromolar inhibition constants, Ki, are identified by this assay and selected for further analysis and development. The ability of test compounds to displace high affinity peptide from the C5a receptor in cellular membrane preparations expressing the receptor is an indication of that compound's ability to inhibit or mimic C5a activation of the receptor in vivo. Subsequent biological screening of the compounds identified in this manner by methods well known in the art, including but not limited to those mentioned above and further described below, then allows classification of the compounds as agonists, partial agonists, or as antagonists.

High affinity binding, as used herein, means a peptide having an affinity for the C5a receptor in the submicromolar range. Preferably in order to identify compounds with a high specificity for the C5a receptor, peptides having affinities in the low nanomolar range are used in the assay. In addition, the peptide should be labeled in some fashion so that specific binding of the peptide is easily quantitated. Any method known in the art may be used for this purpose and those of ordinary skill in the art will appreciate that the teachings disclosed herein should not be construed as limiting on the possible labeling choices. By way of example, fluorescent moieties or radioactive moieties may be used to label the peptides. Because of the very high specific activity achievable using $^{125}$Iodine, ($^{125}$I) labeled peptides, this label is preferred. For this purpose, it is convenient to provide an amino-terminal Tyr residue which may be directly iodinated. Alternatively, the Bolton-Hunter reagent may be used. This reagent is commercially available from many sources, including Sigma Chemical Company, (catalog number H 1256, 3-(p-hydroxyphenyl)propionic acid N-hydroxysuccinimide ester), which imparts a 3-(p-hydroxyphenyl)propionyl group (referred to herein as BH) to the amino terminus of the peptide which is iodinated.

Although any peptide exhibiting high affinity binding to the C5a COOH terminal binding site on the C5a receptor may theoretically be used to advantage in the assay of this invention, in practice, we have encountered and surmounted some difficulties. One difficulty relates to the "stickyness" (also referred to as non-specific binding and insolubility) of labeled peptides for use in the method. Another problem relates to the susceptibility of the peptides to proteolysis. We have been able to identify compounds that overcome both of these problems as follows.

Initially, we attempted to conduct binding studies with $^{125}$I radiolabeled C009: $^{125}$I-Tyr Phe Lys Ala Cha Cha Leu dPhe Arg, SEQ.ID:1:, wherein Cha is cyclohexylalanine, and dPhe is the D isomer of phenylalanine. This compound is a C5a agonist displaying a Ki for C5a of 8 nM. The presence of the tyrosine allowed us to radioiodinate the peptide and establish a binding assay in which both C5a ($IC_{50=0.1}$ nM) and unlabeled C009 ($IC_{50}$=10 nM) inhibit the binding of $^{125}$I-C009 with concentration dependencies similar to those obtained from competition experiments against $^{125}$I-C5a. Moreover, we found that the competition is specific since neither the chemotactic peptide N-formyl-methionyl-leucyl-phenylalanine (fMLP) nor the chemokine IL-8 inhibit the binding of $^{125}$I-C009.

Figure 4A:
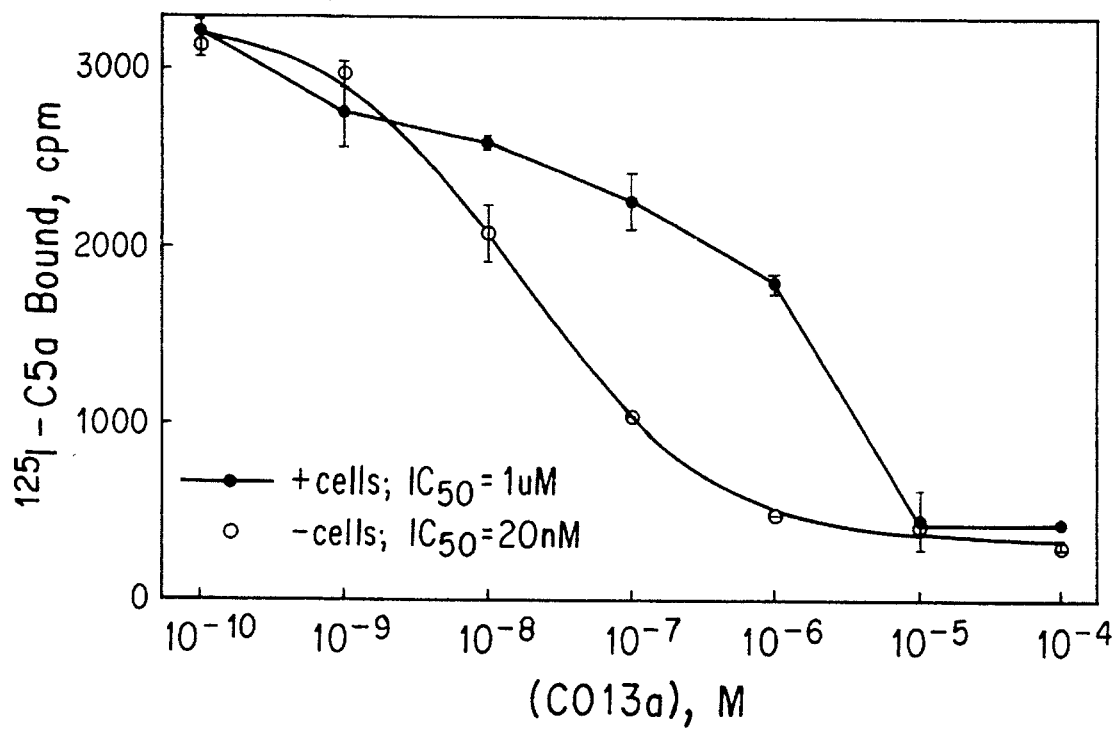
FIGS. 4A, 4B and 4C. (A) Competition binding curve using $^{125}$I-labeled intact C5a and unlabeled C013 peptide in the presence and absence of protease secreting cells.
Figure 4B:
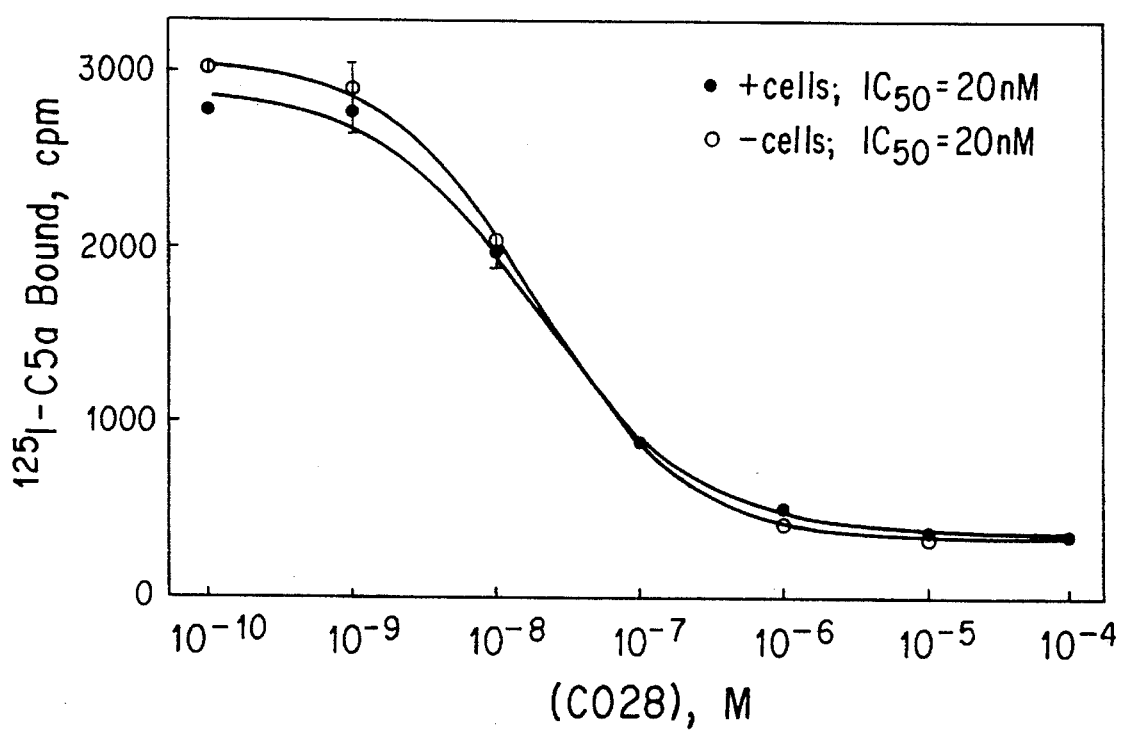
Figure 4C:
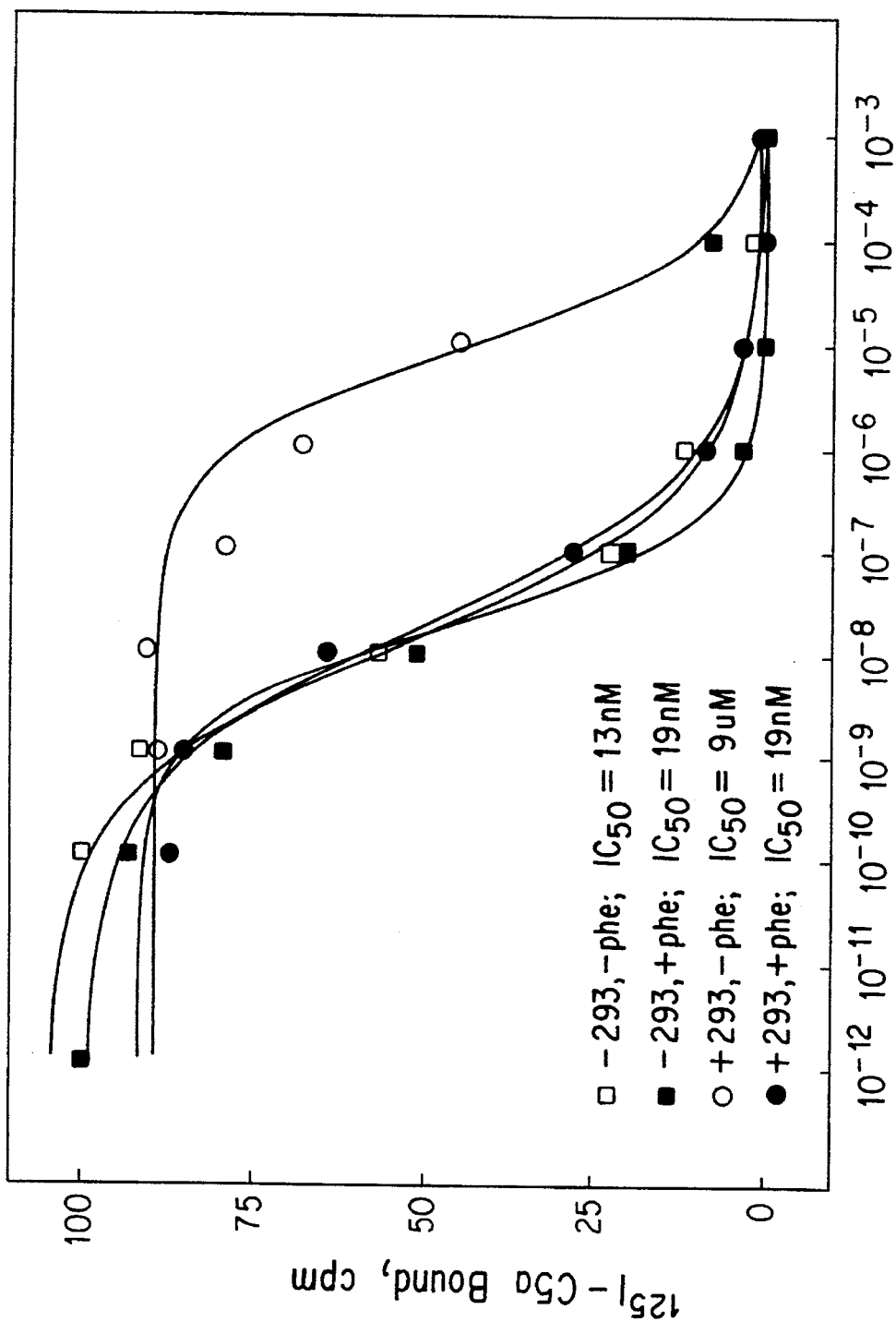

Our efforts to use a binding assay dependent on $^{125}$I-C009, however, were frustrated by both of the problems noted above, namely, high non-specific binding and proteolytic susceptibility of the labeled peptide. In addition, we found that radioiodination of the C009 peptide resulted in about a four-fold loss in binding affinity. We therefore attempted, and succeeded, to improve on this radioligand by identifying a compound with lower non-specific binding, and higher binding affinity. We developed the compound C013, $^{125}$I-Tyr Phe Lys Ala Cha Gly Leu dPhe Arg, SEQ.ID:2:, which had about 30-fold the binding affinity of $^{125}$I-C009. However, this compound was subject to proteolytic degradation (see FIGS. 4A–4C). In FIG. 4A, we discovered that in the displacement of $^{125}$I-C5a from PMN membranes by unlabeled C013a (C013a =C013 minus the amino terminal Tyr), the displacement curve is shifted substantially to the fight (about 100 fold lower potency, ie. 100×lower $IC_{50}$) in the presence of 293 cells, which are known to secrete proteases. In FIG. 4C, we demonstrate that this lowered potency of C013a is eliminated if the protease inhibitor phenanthroline was added to the assay, or if 293 cells were not present.

We therefore determined to discover a radioligand for the assay with superior proteolytic stability and discovered that C028, MePhe Lys Pro dCha Cha dArg, SEQ.ID:3:, demonstrated this important quality. In FIG. 4B, as opposed to C013, there is no shift in the displacement of $^{125}$I-C5a in the presence of 293 cells. We prepared a radioiodinated compound, C064, $^{125}$I-Tyr Phe Lys Pro dCha Cha Arg, SEQ.ID:4:, which retained the proteolytic resistance and low non-specific binding properties of C028.

In the description that follows, it will be recognized by those skilled in the art that unless otherwise specified, an amino acid is the naturally occurring L-amino acid. Where stereochemistry is indicated, this is either by insertion of the letter "L" or "D-" or "d" before the affected amino acid. Furthermore, those skilled in the art will recognize that wherever the amino acid Cha (cyclohexylalanine) appears, another, highly lipophilic residue such as, but not limited to, cyclopentylalanine, cycloheptylalanine, or biphenylalanine may be used. It will also be obvious to those skilled in the art from the description that follows that while a minimum active peptide length appears to be a hexamer, peptides considerably longer, up to even a large peptide (naturally occuring C5a has 74 amino acids) might be used for the purposes we disclose below. For example, multiple inocuous amino acids, such as alanine or glycine residues, could be appended to the amino-terminal portion of the disclosed active peptides with the expectation that little loss in activity would occur. For this purpose, the residue $R^2$ is disclosed which may simply be a peptide bond between $R^1$ and the Phe residue, or it may be a single amino acid, or multiple amino acids, provided that no diminution in C5a receptor binding affinity occurs due to the inclusion of these additional, non-essential amino acids. It should be cautioned that addition of amino acids at this position, while clearly not outside the instant invention, might lead to increased non-specific binding in the competitive assay method of this invention. It should also be understood that the hexamers, heptamers and octamers we disclose are preferred. In the terminology used below, descriptions of peptides as hexamers, heptamers or octamers, the $R^1$ and $R^2$ residues are not included in counting the number of residues in the peptide.

From the foregoing studies, we have therefore been able to define a class of labeled peptides which are useful in the instant method. These compounds have the general formula, SEQ.ID:5:

$$R^1\text{-}R^2\text{-Phe-Lys-}R^3\text{-}R^4\text{-}R^5\text{-}R^6\text{-}X_1\text{-}X_2$$

wherein:

the position occupied by Phe may instead be occupied by 1- or 2-naphthylalanine, Nal;

$R^1$ is an amino acid which permits labeling of the peptide and is preferably Tyr, which allows radioiodination directly, or, equally preferable, is a 3-(4-hydroxyphenyl)propionyl moiety, referred to herein as "BH";

$R^2$ may be a single amino acid or multiple amino acids, provided that no diminution of C5a receptor binding affinity results through inclusion of the one to multiple amino acids at this position; in one embodiment of this invention, this position is merely a peptide bond between $R^1$ and the Phe;

$R^3$ is an amino acid selected from Ala, Pro, Pip (pipecolic acid, also known as homoproline), N-MeAla, and Tic, wherein Tic is tetrahydroisoquinolyl;

$R^4$ is an amino acid selected from L-Cha and D-Cha;

$R^5$ is an amino acid selected from Gly, Cha, Leu, Phe, Nal (wherein Nal is 1- or 2-naphthylalanine), and Trp;

$R^6$ is an L- or D-aliphatic or aromatic amino acid, preferably selected from Leu, D-Arg, Trp, or D-Leu;

$X_1$ is an aliphatic or aromatic D-amino acid provided that $X_2$ is L-Arg and $R^6$ is an L-aliphatic or L-aromatic amino acid such as L-Leu or L-Trp; in this event $X_1$ is preferably selected from D-Phe or D-Ala;

$X_1$ and $X_2$ are not present when $R^6$ is D-Arg; and $X_1$ is D-Arg and $X_2$ is not present when $R^6$ is a D-aliphatic or D-aromatic amino acid, such as D-Leu, or D-Trp.

In preferred embodiments of this invention, $R^1$ is $^{125}$I-Tyr or $^{125}$I-BH, $R^2$ is merely the peptide bond between $R^1$ and Phe, and the segment $R^3$-$R^4$-$R^5$-$R^6$-$X_1$-$X_2$ is selected from any of the following segments, or is an obvious variant of any of the following segments:

-Ala-Cha-Gly-Leu-D-Phe-Arg, SEQ.ID:6:::; -Pro-D-Cha-Cha-D-Arg, SEQ.ID:7:; -N-Me-Ala-D-Cha-Leu-D-Arg, SEQ.ID:8:; -Tic-D-Cha- Phe-D-Arg, SEQ.ID:9:; -Tic-D-Cha-Nal-D-Arg, SEQ.ID: 10:; -Tic-D- Cha-Trp-D-Arg, SEQ.ID: 11:; or -Tic-Cha-Gly-Trp-D-Ala-Arg, SEQ.ID:12:.

Specific compounds within this class are:

SEQ. ID:2: Tyr Phe Lys Ala Cha Gly Leu dPhe Arg, named herein C013;

SEQ. ID:4: Tyr Phe Lys Pro dCha Cha dArg, named herein C064;

SEQ.ID:13: BH-Phe Lys Pro dCha Trp dArg, named herein C147; wherein:
BH is 3-(p-hydroxyphenyl)propionyl;
Cha is cyclohexylalanine,
dCha is the D isomer of cyclohexylalanine,
dPhe is the D isomer of phenylalanine, and
dArg is the D isomer of arginine.

The affinity of these peptides is shown, for example, by radiolabeling intact C5a, and using the unlabeled peptide to compete the labeled C5a from C5a receptor binding sites on cellular membranes. Preparations of polymorphonuclear leukocytes (PMN's) are known to express the C5a receptor, (inhibition of the chemotactic response to C5a of this type of cell is one desirable utility for compounds identified by the instant assay). One method for preparing these membranes is described by Rollins, T. E. et al., [J. Biol. Chem. 264:520–526 (1988); see also U.S. Pat. No. 5,177,190, herein incorporated by reference as a method for isolating and purifying C5a receptor]. Briefly, this involves isolating PMN's in large quantity, disrupting these cells and obtaining the membrane fraction by centrifugation. Protein assay of the membrane preparation allows for standardization of the amount of protein added in any set of membrane binding experiments.

Figure 1:
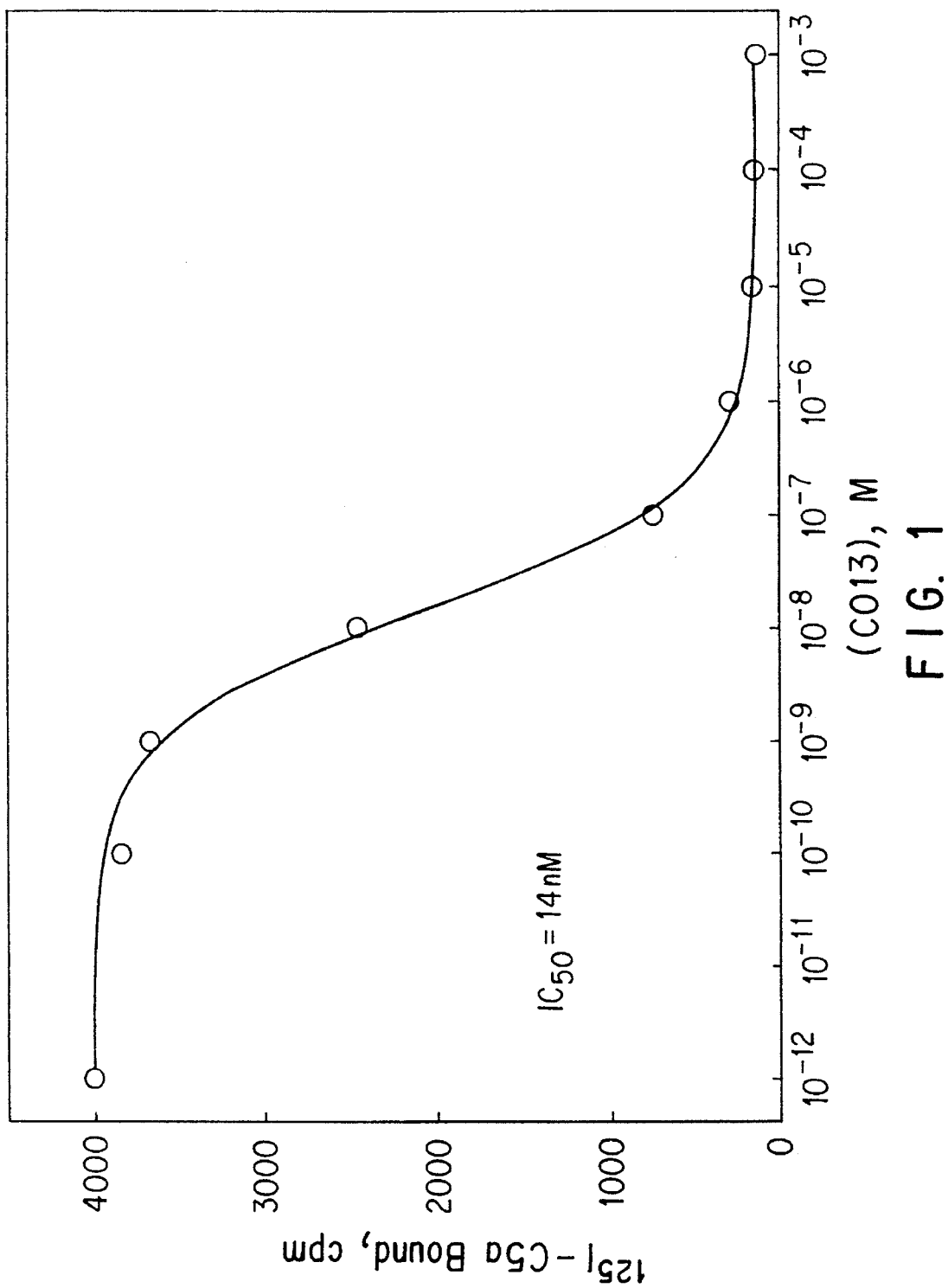
FIG. 1. Competition binding curve using $^{125}$I-labeled intact C5a and unlabeled C013 peptide.
Figure 3A:
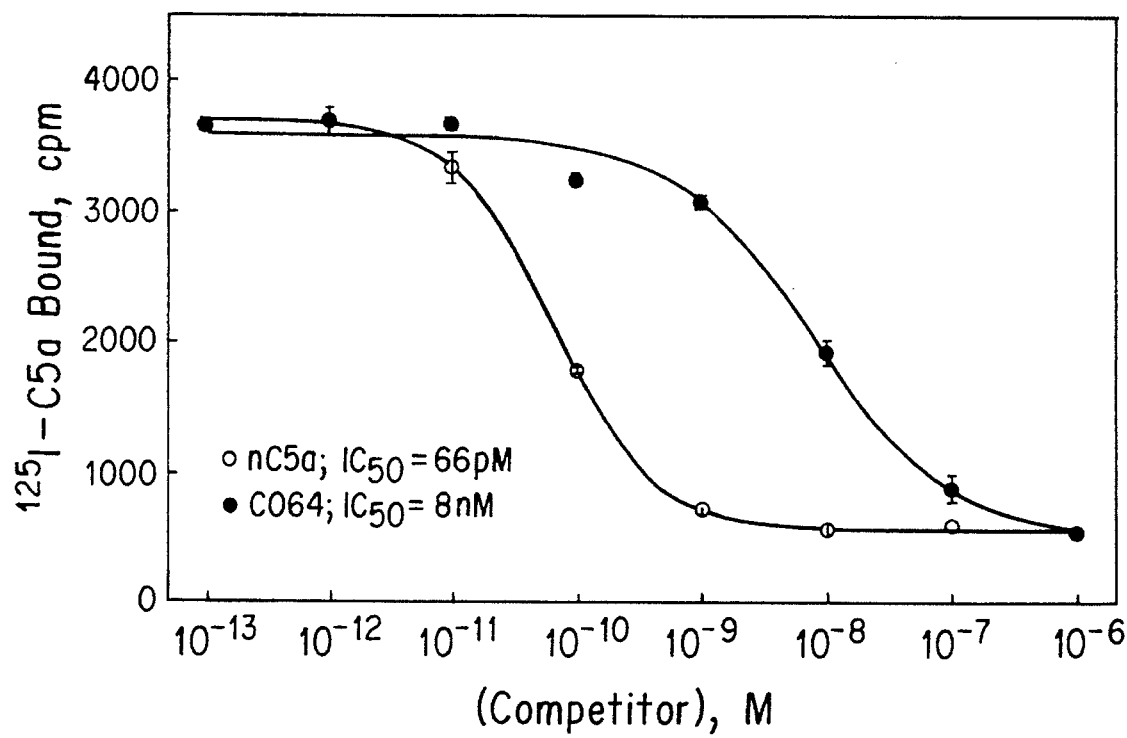
Figure 3B:
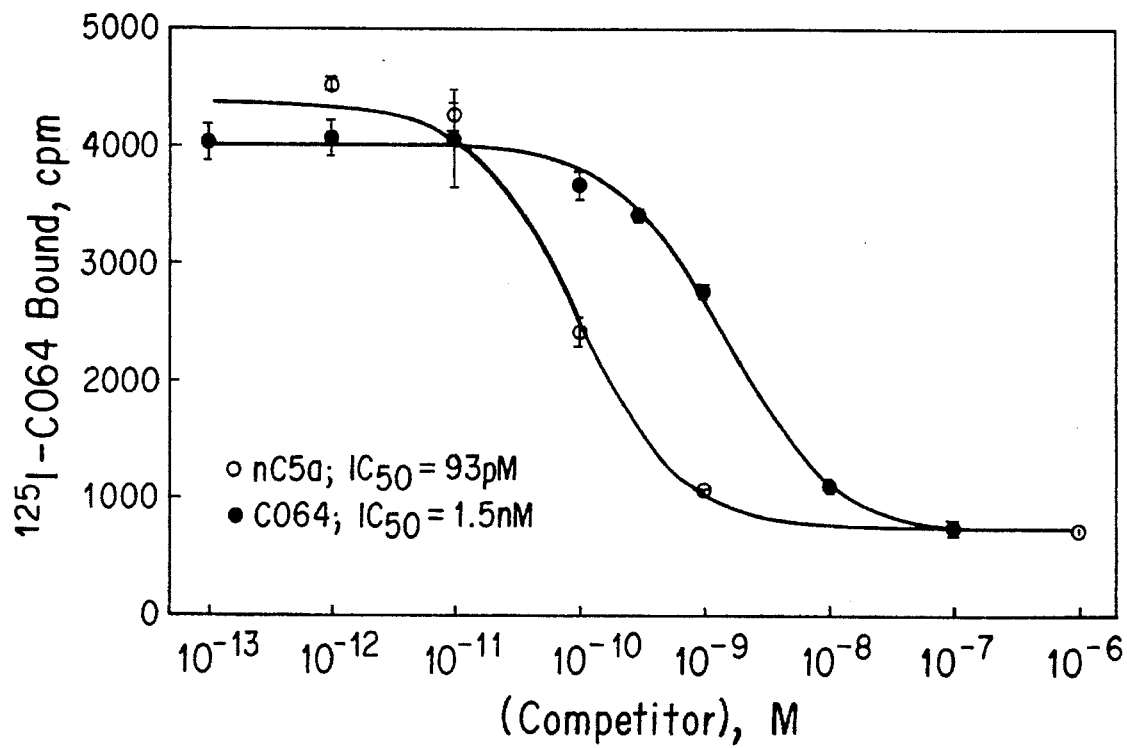

Competition assays for C013 and C064 are shown in FIGS. 1–3. In FIG. 1, unlabeled C013 is used to compete with $^{125}$I-labeled C5a. From that figure, an $IC_{50}$ of this compound is shown to be 14 nM. In FIG. 2, the C013 is $^{125}$I labeled. Unlabeled C5a and unlabeled C013 are each used to compete the labeled C013 from C5a binding sites on the membranes. From this figure, the $IC_{50}$ of C5a is shown to be 0.15 nM, while that of C013 is 1 nM,. In FIG. 3a, $^{125}$I-C5a is competed from its binding site by unlabeled C064 and unlabeled, natural C5a (as opposed to recombinant C5a, which, however, may also obviously may be used for these purposes). From this figure, an $IC_{50}$ of C064 is shown to be 8 nM while that of nC5a is 66 pM. In FIG. 3b, the inverse experiment is shown, wherein $^{125}$I-C064 is displaced by unlabeled C064 and unlabeled nC5a. An $IC_{50}$ of 1.5 nM and 93 pM are derived, respectively. These data are summarized in table I:

TABLE I

| Labeled Ligand | $IC_{50}$ Exhibited by the Unlabeled Ligand | | |
|---|---|---|---|
| | C5a | C013 | C064 |
| C5a | 66 pM | 14 nM | 8 nM |
| C013 | 150 pM | 1 nM | — |
| C064 | 93 pM | — | 1.5 nM |

Thus, we have defined a competitive binding method for determining the binding affinity of a test compound for the C5a receptor and thereby identifying compounds having C5a antagonist, agonist, and partial agonist activity, which comprises:

a. labeling a COOH-terminal C5a peptide analog capable of binding the C5a receptor with submicromolar affinity using an easily quantifiable label;

b. adding a known concentration of said labeled peptide to at least one receptacle either containing membranes enriched in the C5a receptor, or to which membranes enriched in the C5a receptor are subsequently added;

c. adding a known dilution of a test compound in a vehicle, or vehicle alone absent said test compound as a control, to the same receptacle of step (b), simultaneous with, immediately prior to, or immediately after addition of said labeled peptide and said membranes enriched in the C5a receptor, thus creating a mixture of membranes, labeled peptide, and test compound or vehicle absent the test compound; and d. quantitating the percent inhibition of binding of said labeled C5a peptide analog induced by said test compound thereby defining the binding affinity of said test compound. It will be understood by those skilled in the art that, preferably, a series of receptacles is used for this method, each of which is loaded with the same amount of C5a receptor enriched membranes, labeled C5a peptide analog, but differing, known concentrations of test compound. In each case, the amount of labeled peptide remaining bound after washing away unbound labeled peptide is compared with the amount of labeled peptide remaining bound where only vehicle, absent the test compound, is used. Usually, a reasonably accurate inhibition constant for a given test compound may be determined by using a series of between about one and fifteen, and often only three to six concentrations of the test compound. It will also be understood by those skilled in the art that there may be advantages either in first adding membranes to the receptacle, then adding test compound, and only then adding labeled peptide. Alternative orders of addition are clearly within the scope of this invention and could be best optimized by routine testing using different component addition regimens.

The method of this invention further comprises confirming the biological activity of identified compounds using the identical steps as described above, except that labeled, intact C5a is used instead of labeled peptide in step a. Additional biological testing, including inhibition of peripheral blood monocyte degranulation, inhibition of myeloperoxidase release from neutrophils, inhibition of intracellular calcium flux, inhibition of GTPase or GTPγ-S binding, is then used to define said compounds as agonists, partial agonists, or antagonists of C5a.

From the foregoing data, it was possible to proceed with this new assay to identify C5a antagonists by their ability to displace the labeled, high-affinity peptides. We hereby disclose hexapeptide analogs of the form NMePhe-Lys-Pro-dCha-X-dArg, SEQ.ID:15: in which increasing aromaticity at position X leads to a progressive loss of agonism with little change in binding affinity. The different responses induced by C5a are lost in the order: degranulation before $Ca^{2+}$-flux before chemotaxis. We also describe the first compound which acts as a full antagonist of C5a at submicromolar concentrations, as the peptide in which X=Trp. This compound is not only devoid of all agonist properties, but it inhibits C5a induced degranulation and C5a stimulated G protein activation.

Hexapeptides within this class differing only at position X have similar affinities for the C5a receptor. As measured in competition binding experiments against $^{125}$I-C5a on human neutrophil membranes their $IC_{50}$'s varied by only a factor of 3, from 25 to 80 nM (Table II):

TABLE II

Structure and properties of the hexapeptides, SEQ. ID: 15:
NMePhe—Lys—Pro—dCha—X—dArg—COOH

| Peptide | X[1] | Binding[2] $IC_{50}$, nM | Agonist Activity[3] | | | |
|---|---|---|---|---|---|---|
| | | | MPO release | $Ca^{2+}$-flux | chemotaxis | GTPase, |
| C5a | | 0.03 | ++ | ++ | ++ | ++ |
| C028 | Cha | 25 | ++ | ++ | ++ | ++ |
| C068 | Leu | 60 | ++ | ++ | ++ | ++ |
| C026 | Phe | 50 | + | + | ++ | ++ |
| C061 | Nal | 80 | − | +/− | + | + |
| C089 | Trp | 70 | − | − | − | − |

[1]This is the residue which is in the fifth position of the hexapeptide.
[2]Binding experiments were carried out with human neutrophil membranes by competition against $^{125}$I-C5a.
[3]++ signifies full activity, + about 50% of full activity, +/− slight activity, and − no activity. The actual data is presented in the figures.

Hexapeptides in which residue X is aliphatic (either Cha or Leu) are full agonists. Substitution with Phe diminishes by half the peptide's ability to stimulate degranulation or an increase in intracellular $Ca^{2+}$ level, but is without effect on its chemotactic activity. A further increase in aromaticity by introduction of a Nal (naphthylalanine) residue totally abolishes degranulation, nearly eliminates the $Ca^{2+}$ flux, but has only a small effect on chemotaxis. Substitution with Trp generates a peptide (C089, SEQ;ID:13:) that is without agonist activity in any of the assays. Moreover, C089 does not stimulate G protein activation, confirming that the peptide lacks all agonist properties. In fact, C089, is a functional C5a antagonist, as it inhibits C5a stimulated degranulation and G protein activation.

From this invention, it can now generally be stated that a compound that has any $EC_{50}/IC_{50}$ ratio in a continuum from about one to a very large number, approaching infinity as the compound approaches perfect antagonism, is achievable. The $EC_{50}$ measures the concentration of compound at which a 50% maximal stimulation of a given biological response induced by C5a is achieved (chemotaxis, MPO release, calcium flux, GTPase activity or GTPγ-S binding), and the $IC_{50}$ is the concentration at which 50% maximal inhibition of C5a binding is achieved. Thus, for C089, this ratio would be essentially infinite for all of the indicated biological responses as all concentrations tested for this compound, up to and including 100 μM do not induce a response. However, this compound retains excellent ability to inhibit C5a binding (i.e., high receptor binding affinity). On the other hand, a compound such as C028 or C068 could be chosen for its particular utility as almost complete agonists of all of these responses. Alternatively, a partial agonist, such as C026, ($EC_{50}/IC_{50}$=20 for degranulation/binding) could be chosen as a partial agonist for degranution induction but as a full agonist in chemotaxis or C5a receptor-linked G-protein activation, depending on what is required for a particular therapeutic regimen. C089 is the first compound reported exhibiting an $EC_{50}/IC_{50}$>20 for all of the following: C5a induced chemotaxis, MPO release, calcium flux, GTPase activity and GTPγ-S binding.

It is generally believed that an antagonist fails to make one or more specific interactions necessary to activate the receptor. It is interesting to note that there is no correlation between the binding affinities of the 5 hexapeptides and their functional properties. In fact, the spread of affinities between all 5 is only 3-fold, or a difference in binding energy of less than 0.3 Kcal/mole. If a 'triggering' interaction has been lost in C089 it has either been precisely compensated for, or receptor activation is a very low energy event. Since new compensating interactions would have to account for the properties of all five peptides the former hypothesis appears to be unlikely. The C5a receptor differs from most members of the rhodopsin superfamily as it is coupled to its G protein(s) even in the absence of ligand (Siciliano, S. J., Rollins, T. E. and Springer, M. S. (1990) *J. Biol. Chem.* 265, 19568–19574; Rollins, T. E., Sicliano, S., Kobayashi, S., Cianciarulo, D. N., Bonilla-Argudo, V., Collier, K. and Springer, M. S. (1991) *Proc. Natl. Acad. Sci. USA* 88, 971–975.). Thus activation of the C5a receptor may inherently be a simpler process than activation of other family members, a concept which is consistent with the idea of a low energy triggering event. Further support for this hypothesis comes from the observation that it has been much easier to develop C5a agonists than antagonists. An alternative explanation for the loss of agonism is that rather than failing to make the precise interaction necessary to trigger the receptor, C089 blocks the conformational change the receptor must undergo in order to activate the appropriate G protein(s).

It is interesting to note that C061 exhibits good chemotactic activity, even though it generates only a very small increase in intracellular $Ca^{2+}$ levels. This observation is consistent with previous conclusions that the chemotactic response is $Ca^{2+}$ independent (Smolen, J. E., Korchak, H. M. and Weissman, G. (1981) *Biochem. Biophys. Acta* 677, 428–444). It is also evident that the different functional activities generated by receptor activation are lost in a definite order: degranulation before $Ca^{2+}$-flux, before chemotaxis. It has been shown with the fMLP receptor that increasing levels of receptor occupancy also stimulates different responses in a definite order: cell polarization and actin polymerization (chemotaxis) before $Ca^{2+}$-flux, before degranulation (Sklar, L. A., Hyslop, P. A., Oades, Z. G., Omann, G. M., Jesaitis, A. J., Painter, R. G. and Cochrane, C. G. (1985) *J. Biol. Chem.* 260, 11461–11467). As the agonist activity of a ligand decreases, the responses should be lost in the inverse of this order, and that is what is observed. Alternatively, different responses may be transduced by different G proteins. Regardless of which explanation is correct, the five hexapeptides are powerful tools for probing the transduction mechanism(s) which underlie the different functional responses.

Finally, C089 demonstrates that full antagonists of the C5a receptor can be generated and this provides an opportunity for further studies on the role of C5a in both host-defense, and inflammatory disorders.

It is predictable from this disclosure that peptides displaying the appropriate aromaticity at the correct position in the C5a COOH-terminal binding site of the C5a receptor will act as antagonists. Thus, hexapeptides, and obvious variants thereof, of the form, SEQ.ID:14::

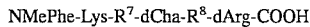

wherein:

$R^7$ is Pro or Tic;

$R^8$ is Phe, Nal, Trp or another more aromatic amino acid derivative, act as full antagonists, while peptides having lower aromaticity at the $R^8$ position are useful as partial or complete agonists. It should also be noted that in the foregoing compound, the N-methyl group on the Phe may be absent. Furthermore, the NMePhe may be replaced with a Nal residue (1-naphthylalanine or 2-naphthylalanine, or an equivalent thereof). In addition, while a hexapeptide appears to be the minimum peptide length that can be used for this purpose, those of skill in the art will recognize that peptides of greater length could display full antagonist activity also. Examples of more aromatic amino acids include, but are not limited to: biphenylalanine; halogenated Trp, for example 5-chloro-Trp; and benzoyl-Phe. Obvious variants of this compound would include amino or carboxy terminal extensions of the peptide, so-called "silent" changes wherein an aliphatic for aliphatic, aromatic for aromatic, lipophilic for lipophilic, anionic for anionic or cationic for cationic residue change is made. It should be understood that aliphatic and aromatic include naturally occurring and non-naturally occuring amino acids.

Compounds identified according to the method of this invention as being C5a antagonists can be used in the treatment of a wide variety of C5a mediated diseases such as acute inflammatory response, including acute respiratory distress syndrome, and anaphylactic shock; chronic inflammation, including rheumatoid arthritis, osteoarthritis, and psoriasis; and the metastatic spread of cancerous tumors.

The compounds identified according to the method of this invention can be used to reduce pain and inflammation, to correct respiratory, cardiovascular and intravascular alterations or disorders, and to regulate the activation or coagulation of the blood platelets, to correct hypertension during shock, the pathogenesis of immune complexes that trigger smooth muscle contraction.

For the treatment of inflammation, arthritic conditions, psoriasis, asthma, or other diseases mediated by leukotrienes, a compound identified according to the method of this invention may be administered orally, topically, parenterally, by inhalation spray or rectally in dosage unit formulations containing conventional non-toxic pharmaceutically acceptable carders, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the an for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate, sodium phosphate; granulating and disintegrating agents, for example, corn starch, or alginic acid; binding agents, for example, starch, gelation or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl disterate may be employed. They may also be coated by the techniques described in the U.S. Pat. Nos. 4,256,108; 4,166, 452; and 4,265,874 to form osmotic therapeutic tablets for control release.

Formulations for oral use may also be presented as hard gelatin capsules wherein the active ingredient is mixed with an inert solid diluent, for example, calcium carbonate calcium phosphate of kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial ester derived from fatty acids and hexitol anhydrides, for example, sorbitan monooleate, and condensation products of the said partial esters with ethylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent and optionally an adjuvant such as diisopropyl adipate, diethy sevacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g. hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated conditions (10 mg to 7 gms per patient per day). For example, leukotriene biosynthesis is effectively treated by the administration from about 0.5 to 50 mg of the compound per kilogram of body weight per day (25 mg to 5 gms per patient per day).

The amount of active ingredient that may be combined with the carrier materials to produce a single dosage will vary depending upon the host treated and the particular mode of administration. Dosage unit forms will generally contain from about 25 mg to about 1 g of active ingredient. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, methods for using the C5a antagonists identified according to this invention comprise contacting the C5a receptor with an antagonistically effective amount of said compound whenever such antagonism is needed. The higher the binding affinity of the compound, the lower the necessary dose usually is.

The following examples illustrate the method of this invention and the preparation of compounds identified according to this method. The examples are not to be construed as limiting the invention set forth in the claims appended hereto.

Materials.

Human C5a was purified as previously reported (Rollins, T. E., Sicliano, S. and Springer, M. S. (1988) *J. Biol. Chem.* 263, 520–526). All Fmoc amino acids and resin supports were purchased from Novabiochem (La Jolla, California). Indo-1 was obtained from Molecular Probes, $Na^{125}I$ from Amersham, Chloramine-T from Baker and $Na_2{}^{51}CrO_4$ from New England Nuclear.

Peptide Synthesis.

The peptides were synthesized on a Milligen/Biosearch 9500 Synthesizer (Burlington, Mass.) by standard Fmoc/DIPCIDI chemistry. The resin bound peptides were cleaved by Reagent R (90% TFA, 5% Thioanisole, 3% Ethanedithiol, 2% Anisole), precipitated into ether and purified by RP-HPLC on a Waters PrepLC 4000 using C-18 columns. Peptide structures were confirmed by Electrospray Ionization Mass Spectrometry (Finnigan Corp., San Jose, Calif.).

EXAMPLE 1

PREPARATION OF C5a COOH-TERMINAL PEPTIDES HAVING HIGH AFFINITY FOR THE C5a RECEPTOR:

Peptides useful in the method of the instant invention may be prepared by standard solid phase peptide synthesis. The synthesis of Tyr Phe Lys Ala Cha Gly Leu dPhe Arg (C013, SEQ.ID:2:) was as follows:

Fmoc-L-Arg(Mtr)-Wang Resin (0.5 mmol) was placed in the reaction vessel of a Milligen/Biosearch 9500 Solid Phase Peptide Synthesizer and the following amino acids were sequentially attached to the resin using DIPCIDI/HoBt coupling and Piperidine deprotection: Fmoc-D-Phe, Fmoc-L-Leu, Fmoc-Gly, Fmoc-L-Cyclohexylalanine, Fmoc-L-Ala, Fmoc-L-Lys(tBoc), Fmoc-L-Phe and Fmoc-L-Tyr (tBu).

Following the synthesis, the peptide-resin was washed with methylene chloride and treated with 15 mL of Reagent R (90% TFA, 5% Thioanisole, 3% Ethanedithiole, 2% Anisole) for 4 to 8 hours. The mixture was then filtered to separate the peptide from the resin, with the peptide being precipitated into diethyl ether. The crude peptide was isolated by filtration and purified by high performance liquid chromatography (HPLC). The purified fractions collected from the HPLC were pooled and lyophilized to a dry amorphous white powder. FAB/MS was used to analyze the final product and the results were consistent with the proposed structure: $(M+H)^+$ at m/z=1154.8.

The peptide C064, SEQ.ID:4:, and other peptides useful in the method of this invention are synthesized in an identical fashion, except that the correct sequence of amino acid monomers is added to the reaction vessel.

EXAMPLE 2

RADIOLABELING OF C5a COOH-TERMINAL PEPTIDES:

Peptide (5 nMoles) are added to 40μL of 0.1 M sodium phosphate, pH 7.6, in a tube, followed by 2 mCi of $^{125}I$ in 20 μL. 10 μL of a freshly made 0.5 mg/mL solution of chloramine T is then added. After 30 seconds of incubation, 10 μL of a freshly prepared 2 mg/mL solution of $Na_2S_2O_3$ is added, the tube is vortexed, and the sample loaded onto a Vydac C4 reverse phase column. The column is developed with a TFA/acetonitrile gradient and the iodinated peptide is isolated. The material is stored at 4° C. in the elution buffer.

Alternatively, compounds that are easily oxidized (such as C089) are radioiodinated using the Bolton-Hunter reagent:

0.5 nmoles [$^{125}I$]-Bolton-Hunter (in benzene) was dried on the bottom of a vial with a stream of $N_2$. To this vial was added 10 moles C147 (protected C089), dissolved in 10 μl of phosphate buffer, pH8.0, and the mixture was incubated for 60 min., at 0° C. 0.2M glycine (in phos. buffer) was added to react unchanged ester for 5 min., at 24° C. 2% hydrazine (in phos. buffer) was then added to deblock the lysine of C147 for 30 min., at 24° C. The radioiodinated peptide was separated from starting materials and recovered by Vydac C4 reverse phase HPLC.

EXAMPLE 3

C5a COOH-TERMINAL PEPTIDES BINDING INHIBITION ASSAY:

Compounds exhibiting C5a receptor affinity are identified as follows:

To 205 µL binding buffer (50 mM HEPES, pH 7.2, containing 5 mM $MgCl_2$, 1mM $CaCl_2$, 0.5% BSA) in a polypropylene tube is added 30,000CPM of the $^{125}I$ peptide in 20 µL, and 5 µL of a known dilution of the test compound or diluent, followed by a 20 µL aliquot of neutrophil membrane [equivalent to 500,000 neutrophils; Rollins, T.E. et al., J. Biol Chem. 260:7157 (1985); see also U.S. Pat. No. 5,177,190, herein incorporated by reference].

The assay mixture is incubated for 2 hours at 29° C. Binding buffer (2 mL) is then added, the tube is vortexed, and the contents filtered over a Wattmann GF/C filter soaked in 0.33% polyethylenimine. An additional aliquot of binding buffer (2 mL) is added to the tube to rinse the tube, and is then used to wash the filter. The filters are removed from the apparatus and counted. Non-specific backgrounds are determined by performing assays in the presence of either 10 nM C5a, or 1 µM unlabeled peptide. Compounds which inhibit the binding of the labeled peptide are considered to be potential active compounds.

EXAMPLE 4

CONFIRMATION OF ABILITY TO INHIBIT BINDING OF INTACT C5a;

One method of confirming the biological activity of the compounds identified according to the method of this invention, exemplified above in Example 3, is measured in terms of their ability to inhibit the binding of intact C5a to PMN membrane.

The C5a binding inhibitor assay is performed in 12×75 mm polypropylene tubes, or another acceptable receptacle including multiwell plates which would allow for automation, as follows: 200 µL of binding buffer (Hanks' balanced salts containing 10 mM HEPES, pH 7.2, 100 µM PMSF, and 0.5% BSA), 20 µL of 125 I-C5a (typically 20 pM final concentration) and either 10 µL of the compound under test, or 10 µL of solvent are combined in the tube. Binding is initiated by an addition of 20 µL of PMN membrane (typically 0.5 µg of protein) to each tube. After incubation for 90 min. at room temperature 2 ml of 0.05 M HEPES, pH 7.2, containing 0.5% BSA are added to the tube, the contents vortexed and filtered over a Whatman GF/C filter which has been soaked in 0.3% polyethylenimine. An additional 2 ml of buffer are added to the tube and used to wash the filter. All of the test samples are dissolved in DMSO, another water miscible organic solvent, or in an aqueous solvent. Non-specific background was determined by inclusion of a 100-fold excess of unlabeled C5a.

The percent inhibition is calculated according to the following formula:

$$\% \text{ Inhibition} = \frac{100 \times CPM_{Sample} - CPM_{Non\text{-}specific\ background}}{CPM_{Solvent} - CPM_{non\text{-}specific\ background}}$$

Iodination of C5a was carded out with the use of chloramine T. (Rollins, T.E., and Springer, M.S. (1985) *J. Biol. Chem.* 260, 7157–7160). The $^{125}I\text{-}C5_a$ (100–200 mCi/mg) produced by this procedure had the same affinity for the receptor as did the nonderivatized protein. Concentrations of C5a were determined by amino acid analysis and by RIA (Amersham Corp.). Membranes were prepared from human PMN as described by Rollins, T.E., Sciliano, S and Springer, M.S., *J. Biol Chem* 264 520–526 (1988).

EXAMPLE 5

CONFIRMATION OF BIOLOGICAL ACTIVITY OF COMPOUNDS AND CLASSIFICATION AS AN AGONIST, PARTIAL AGONIST OR ANTAGONIST OF C5a MEDIATED RESPONSES:

1. Degranulation.
Myeloperoxidase (MPO) Assays.

This assay was performed on human neutrophils as previously reported and it is a measure of C5a or peptide induced exocytosis (Rollins, T. E. and Springer, M. S. (1985) *J. Biol. Chem.* 260, 7157–7160). In assessing the ability of C089 to antagonize stimulated MPO release, the cells were incubated with cytochalasin B for 5 min at 37° C., followed by addition of C089 and 5 min later by either C5a or IL-8.

The functional properties of two of the peptides, C026, and C028, were originally described by Mollison et. al (Mollison, K. W., Krause, R. A., Fey, T. A., Miller, L., Wiedeman, P. e., Kawai, M., Lane, B., Luly, J. R. and Carter, G. W. (1992) *FASEB J.* 6, A2058). These authors reported that while C028 (X=Cha) exhibited normal degranulating activity, C026 (X=Phe) not only failed to stimulate degranulation, it acted as an antagonist for this property. We have reinvestigated the degranulating activities of these peptides as measured by the release of myeloperoxidase (MPO) from human neutrophils. Our results with C028 are consistent with those of Mollison et. al. This molecule is a full agonist for degranulation: not only is the maximal release the same as that produced by C5a (FIG. 5A), but the concentration dependence of the response is as expected. The $EC_{50}/IC_{50}$ (degranulation/binding) for C028 is 8, the same as that measured for C5a (Table II, FIG. 5A). In contrast to the data reported by Mollison et. al., in our hands C026 (X=Phe) retains substantial degranulating activity. As shown in FIG. 5A, C026 generates 50% of the maximal release produced by C5a or C028, with only a slight shift in the expected concentration dependence ($EC_{50}/IC_{50=20}$). However, the difference in activity between C026 and C028 is significant and reproducible. Since the structural difference between the two is the substitution of an aromatic for an aliphatic residue (Phe for Cha) we chose to make additional changes at position 5 which further increased aromaticity. The two new peptides, C061 and C089, have either a 1-naphthylalanine (Nal), or a Trp at position 5. As seen in FIG. 5A both are totally devoid of degranulating activity. To further examine whether the differences in activity between the peptides reflects the increased aromaticity we synthesized a molecule with Leu, an aliphatic amino acid, at position 5 (C068, Table II). This peptide is a full agonist, as measured both by maximal release and $ED_{50}/IC_{50}$ ratio.

2. Stimulated increases in intracellular $Ca^{2+}$ levels.

A second functional response induced by C5a is a transient increase in the level of intracellular $Ca^{2+}$.
Calcium Fluxes Ligand induced $Ca^{2+}$ fluxes were measured by following the change in Indo-1 induced fluorescence on a FACS analyzer as previously described (Van Riper, G., Siciliano, S. J., Fischer, P. A., Meurer, R., Springer, M. S. and Rosen, H. (1993) *J. Exp. Med.* 177, 851–856.).

FIG. 5B compares the maximal effects of each peptide (10–100 μM) with the response induced by C5a (1 nM). C028 and C5a produce comparable elevations in $Ca^{2+}$ level, while C026 generates only 50% of this response. C089 fails to stimulate a detectable change in $Ca^{2+}$ level. However, although greatly reduced relative to the change induced by C5a, C061, does reproducibly generate a small increase in the level of intracellular $Ca^{2+}$. Finally, C068 is a full agonist in this assay.

3. Chemotaxis.

Perhaps the major functional response elicited by C5a is chemotaxis. We have measured the responses to C5a and the peptides using a Boyden Chamber assay:

Chemotaxis Assay

This assay is a modification of the procedure described by Sims et. al. (Sims, T. J., Geissler, F. T. and Page, R. C. (1985) *J. Immunol. Meth.* 78, 279–291). Chemotaxis was assayed in a 48 well Neuro Probe chamber (Neuro Probe, Bethesda, MD) using $^{51}$Cr-labelled cells. Varying concentrations of C5a or peptide were placed in the lower chamber which was successively covered by a 100 μm nitrocellulose membrane (Neuro Probe, Bethesda, Md.) and two 3 μm polycarbonate filters. After preforming a gradient for 30 minutes at 37° C., $2 \times 10^5$ labelled cells were added to the upper chamber and allowed to migrate at 37° C. for one hour. The upper two polycarbonate filters were then discarded and the formed wells cut from the nitrocellulose membrane. The radioactivity present in these filters is a measure of the number of cells that migrated through both polycarbonate filters.

A plot of the initial concentration of agent placed in the lower chamber against the number of cells which migrate (measured by counting the $^{51}$Cr-labelled cells) is shown in FIG. 6A. For C5a, maximal response occurs at 10 nM. Since the cells migrate in response to the concentration gradient established across the filters, the actual stimulatory concentration is much lower than the nominal value plotted on the abcissa in FIG. 6A.

Both C026 and C028 are strong chemoattractants (FIG. 6A). In contrast to the differences in their abilities to stimulate degranulation or induce changes in $Ca^{2+}$-levels, both peptides elicit similar chemotactic responses. The apparent differential activation is even more pronounced with the 1-naphthylalanine peptide, C061. This molecule, which is devoid of degranulating activity, elicits as great an accumulation of cells as either C026, or C028, or for that matter, C5a (FIG. 6A). However, greater concentrations of C061 are necessary. Maximal migration of cells in response to C026 or C028 occurs at 1 μM, while for C061 maximal response is observed at about 100 μM. Similar to its lack of activity in the other assays, C089, shows little or no ability to stimulate a chemotactic response (FIG. 6A).

3. GTPase activity.

Since C5a evokes such a plethora of biological responses, it is difficult to ascertain a molecule's overall functional properties from any subset of responses. In particular, it would be premature to conclude that C089 lacks all agonist activity from data described above. An alternative to investigating all of the responses generated by the C5a receptor, is to determine a molecule's ability to stimulate G protein activation. Such a measurement should give an integrated view of a molecule's agonist properties. As a measure of G protein activation we have investigated the peptides' abilities to stimulate GTPase activity in human neutrophil membranes:

GTPase Assay

The method of Kupper et al. (Kupper, R. W., Dewald, B., Jakobs, K. H., Baggiolini, M. and Gierschik, P. (1992) *Biochem. J.* 282, 429–434) was adapted for use in microtiter plates. Neutrophil membranes were suspended in 50 mM triethanolamine-HCl, 5 mM MES, pH 7.3, containing 1 mM EDTA, 5 mM $MgCl_2$, 143 mM NaCl, 0.16% BSA, 1 mM ouabain, 1 mM AMP-PNP, 0.5 mM ATP, 2.5 U/mL creatine phosphokinase,. 10 mM creatine phosphate, 0.1 mM PMSF and 10 ng/mL each of leupeptin, aprotinin and chymostatin. 50 μL of membranes containing 1–5 μg protein were added to 50 μL of the same buffer containing the test agent and 0.25 μM [$\gamma$-$^{32}$P]-GTP (2,000 cpm/pmol) in the wells of a U-shaped microtiter plate. After incubation for 15–30 rain at 29° C., 100 μL of a 10% (w/v) charcoal suspension in 100 mM $H_3PO_4$ was added and plates were centrifuged at 2000 rpm for 5 min. 100 μL of the supernatant was transferred to an Optiplate microtiter plate and 100 μL of Microscint-40 scintillation cocktail was added. Plates were counted in a Packard TopCount microtiter plate counter.

The concentration dependencies of this activity are shown in FIG. 6B. The peptide C028, which is a full agonist in all of the responses studied stimulates as much GTPase activity as does C5a, and has an $ED_{50}=0.1$ μM. C026 which is as chemotactic as C028, but which has less activity in the other responses measured, shows a somewhat reduced ability to stimulate the GTP hydrolysis. C061, which in general shows less agonist activity than either C028 or C026, has significantly lower GTPase activity as well. The Trp peptide, C089, which has no activity in any of the other assays also fails entirely to stimulate GTP hydrolysis, confirming our suspicions that it is completely devoid of agonist activity. Similar results have been obtained in experiments which monitor ligand stimulated increases in GTPγS binding.

EXAMPLE 6

IDENTIFICATION OF A FULL ANTAGONIST OF C5a: C089 is a C5a antagonist: Since C089 is devoid of agonist activity and inhibits C5a binding, we expected that it would act as a functional antagonist as well. As shown in FIG. 7A, C089 inhibits C5a induced degranulation with an $IC_{50}$ of 0.1 μM. Moreover, this inhibition is specific as it has little effect on IL-8 induced degranulation. C089 also inhibits C5a stimulated GTPase activity with an $IC_{50}$ of 3 μM (FIG. 7B).

What is claimed is:

1. A competitive binding method for determining the binding affinity of a test compound for the C5a receptor and thereby screening for compounds which may have C5a antagonist, agonist, or partial agonist activity, which comprises:

a. labeling a COOH-terminal C5a peptide analog capable of binding the C5a receptor with submicromolar affinity ($K_i$<1 µM) using a quantifiable label, wherein said peptide is selected from the group consisting of:
   (i) $R^1$-$R^2$-Phe-Lys-$R^3$-$R^4$-$R^5$-$R^6$-$X_1$-$X_2$, SEQ.ID:5: wherein:
      $R^1$ is an amino acid which permits labeling of the peptide;
      $R^2$ is the peptide linkage between $R^1$ and Phe, a single amino acid or multiple amino acids, provided that no diminution of C5a receptor binding affinity results through inclusion of the one to multiple amino acids at this position;
      $R^3$ is an amino acid selected from Ala, Pro, Pip, N-MeAla, and Tic;
      $R^4$ is an amino acid selected from L-Cha and D-Cha;
      $R^5$ is an amino acid selected from Gly, Cha, Leu, Phe, Nal and Trp;
      $R^6$ is D-Arg and $X_1$ and $X_2$ are not present; or
      $R^6$ is D-aliphatic or D-aromatic amino acid, $X_1$ is D-Arg, and $X_2$ is not present;
   (ii) Tyr-Phe-Lys-Tic-Cha-Gly-Trp. D-Ala-Arg; and
   (iii) Tyr Phe Lys Ala Cha Gly Leu dPhe Arg, SEQ.ID:2;

b. adding a known concentration of said labeled peptide to at least one receptacle either containing membranes enriched in the C5a receptor, or to which membranes enriched in the C5a receptor are subsequently added;

c. adding a known dilution of a test compound in a vehicle, or vehicle alone absent said test compound as a control, to the same receptacle of step (b), simultaneous with, immediately prior to, or immediately after addition of said labeled peptide and said membranes enriched in the C5a receptor, thus creating a mixture of membranes, labeled peptide, and test compound or vehicle absent the test compound; and d. quantitating the percent inhibition of binding of said labeled C5a peptide analog induced by said test compound thereby defining the binding affinity of said test compound.

2. The method of claim 1 which further comprises confirming the binding affinity of compounds identified according to the method of claim 1 which comprises repeating the steps of claim 1 with the proviso that in step a, labeled, intact C5a is used instead of a labeled C5a peptide analog.

3. The method of claim 1 which further comprises biological testing to define said test compound as an agonist, partial agonist, or antagonist of C5a.

4. The method of claim 3 wherein said biological testing is selected from the group consisting of:
   inhibition of peripheral blood monocyte degranulation, inhibition of myeloperoxidase release from neutrophils, inhibition of intracellular calcium flux, inhibition of GTPase binding and inhibition of GTPγ-S binding.

5. The method of claim 1 wherein $R^6$ of said peptide in step (a) is D-Leu or D-Trp, $X_1$ is D-Arg, and $X_2$ is not present.

6. The method of claim 1 wherein:

$R^1$ is $^{125}$I-Tyr or $^{125}$I-BH, $R^2$ is the peptide linkage between $R^1$ and the Phe, and the segement $R^3$-$R^4$-$R^5$-$R^6$-$X_1$-$X_2$ is selected from any of the following segments: -Ala-Cha-Gly-Leu-D-Phe-Arg, SEQ.ID:6:; -Pro-D-Cha-Cha-D-Arg, SEQ.ID:7:; -N-Me-Ala-D-Cha-Leu-D-Arg, SEQ.ID:8:; -Tic-D-Cha-Phe-D-Arg, SEQ.ID:9:; -Tic-D-Cha-Nal-D-Arg, SEQ.ID: 10:; -Tic-D-Cha-Trp-D-Arg, SEQ.ID: 11:; or -Tic-Cha-Gly-Trp-D-Ala-Arg, SEQ.ID:12:.

7. The method of claim 1 wherein the peptide of step (a) is a radioiodinated derivative of:

SEQ. ID:2: Tyr Phe Lys Ala Cha Gly Leu dPhe Arg;

SEQ. ID:4: Tyr Phe Lys Pro dCha Cha dArg; or

SEQ.ID:13: BH-Phe Lys Pro dCha Trp dArg.

* * * * *